(12) United States Patent
Yamazaki et al.

(10) Patent No.: US 10,923,764 B2
(45) Date of Patent: Feb. 16, 2021

(54) ELECTROLYTE SOLUTION, ELECTROCHEMICAL DEVICE, LITHIUM ION SECONDARY BATTERY, AND MODULE

(71) Applicants: DAIKIN INDUSTRIES, LTD., Osaka (JP); TOYOTA JIDOSHA KABUSHIKI KAISHA, Toyota (JP)

(72) Inventors: Shigeaki Yamazaki, Osaka (JP); Shinichi Kinoshita, Osaka (JP); Hiroto Asano, Toyota (JP); Toshiyuki Kawai, Toyota (JP)

(73) Assignees: DAIKIN INDUSTRIES, LTD., Osaka (JP); TOYOTA JIDOSHA KABUSHIKI KAISHA, Toyota (JP)

( * ) Notice: Subject to any disclaimer, the term of this patent is extended or adjusted under 35 U.S.C. 154(b) by 182 days.

(21) Appl. No.: 15/841,616

(22) Filed: Dec. 14, 2017

(65) Prior Publication Data

US 2018/0183097 A1 Jun. 28, 2018

(30) Foreign Application Priority Data

Dec. 26, 2016 (JP) .............................. JP2016-251176

(51) Int. Cl.
| | | |
|---|---|---|
| *H01M 10/0569* | (2010.01) | |
| *H01M 10/0564* | (2010.01) | |
| *H01M 10/0567* | (2010.01) | |
| *H01M 10/0525* | (2010.01) | |
| *C07D 307/60* | (2006.01) | |

(52) U.S. Cl.
CPC ... *H01M 10/0564* (2013.01); *H01M 10/0525* (2013.01); *H01M 10/0567* (2013.01); *H01M 10/0569* (2013.01); *C07D 307/60* (2013.01)

(58) Field of Classification Search
CPC ......... H01M 10/0569; H01M 10/0567; H01M 10/0564; H01M 10/0525; H01M 10/0566; C07D 307/60
See application file for complete search history.

(56) References Cited

U.S. PATENT DOCUMENTS

| | | |
|---|---|---|
| 2007/0224516 A1 | 9/2007 | Deguchi et al. |
| 2010/0035162 A1 | 2/2010 | Chiga et al. |
| 2010/0081062 A1 | 4/2010 | Chiga et al. |
| 2012/0219866 A1 | 8/2012 | Onuki et al. |
| 2013/0130128 A1 | 5/2013 | Okamoto et al. |
| 2013/0266847 A1 | 10/2013 | Noguchi et al. |
| 2014/0248529 A1 | 9/2014 | Chen et al. |
| 2015/0380769 A1 | 12/2015 | Chiga et al. |
| 2016/0285131 A1 | 9/2016 | Yamauchi et al. |
| 2016/0308252 A1* | 10/2016 | Iriyama ............. H01M 10/0569 |
| 2017/0040608 A1* | 2/2017 | Asano ............... H01M 10/0569 |
| 2018/0183105 A1 | 6/2018 | Asano et al. |

FOREIGN PATENT DOCUMENTS

| | | |
|---|---|---|
| CN | 101030661 A | 9/2007 |
| CN | 105556729 A | 5/2016 |
| JP | 2005-317446 A | 11/2005 |
| JP | 2008-257988 * | 4/2007 |
| JP | 2007-250415 A | 9/2007 |
| JP | 2008-257988 A | 10/2008 |
| JP | 2009-289414 A | 12/2009 |
| JP | 2010-062132 A | 3/2010 |
| JP | 5115109 B2 | 1/2013 |
| JP | 2015-179680 A | 10/2015 |
| JP | 2015-191738 A | 11/2015 |
| JP | 2016-027548 A | 2/2016 |
| JP | 2016-519400 A | 6/2016 |
| KR | 10-2015-0138326 A | 12/2015 |
| WO | 2011/025016 A1 | 3/2011 |
| WO | 2012/017999 A1 | 2/2012 |
| WO | 2012/077712 A1 | 6/2012 |
| WO | 2014/165748 A1 | 10/2014 |

OTHER PUBLICATIONS

R. Chandrasekaran et al: "Effect of Fluoroadditives on the Electrode Characteristics of Graphite for Secondary Lithium Battery", Journal of New Materials for Electrochemical Systems 9, 2006, pp. 181-189. (9 pages total).

K. Sato et al: "Mixed Solvent Electrolytes Containing Fluorinated Carboxylic Acid Esters to Improve the Thermal Stability of Lithium Metal Anode Cells", Solid State Ionics, vol. 148 (2002), pp. 463-466. (4 pages total).

Office Action issued by the USPTO dated Oct. 16, 2019 in U.S. Appl. No. 15/834,235.

U.S. Appl. No. 15/834,235, filed Dec. 7, 2017.

Communication dated Feb. 4, 2020, from the United States Patent and Trademark Office in U.S. Appl. No. 15/834,235.

Yamaki et al., "Thermal studies of fluorinated ester as a novel candidate for electrolyte solvent of lithium metal anode rechargeable cells", Journal of Power Sources, vol. 102, 2001, pp. 288-293 (6 pages).

(Continued)

*Primary Examiner* — Laura Weiner

(74) *Attorney, Agent, or Firm* — Sughrue Mion, PLLC

(57) ABSTRACT

The present invention provides an electrolyte solution in which a decrease in capacity retention is suppressed and an increase in gas production is suppressed even when stored at high temperatures. Provided is an electrolyte solution containing: a compound (1) represented by formula (1): $CF_3CFX^{11}COOR^{11}$, wherein $X^{11}$ is a hydrogen atom, a fluorine atom, or a C1-C3 alkyl group in which hydrogen atoms are optionally replaced by fluorine atoms, and $R^{11}$ is a C1-C3 alkyl group in which hydrogen atoms are optionally replaced by fluorine atoms; a fluorinated carbonate; and a cyclic acid anhydride.

5 Claims, No Drawings

(56) References Cited

OTHER PUBLICATIONS

Final Office Action dated Aug. 6, 2020, from the United States Patent and Trademark Office in related U.S. Appl. No. 15/834,235.
Non-Final Office Action dated May 1, 2020, from the United States Patent and Trademark Office in related U.S. Appl. No. 15/834,235.
Notice of Allowance dated Nov. 20, 2020, from the United States Patent and Trademark Office in related U.S. Appl. No. 15/834,235.

* cited by examiner

ELECTROLYTE SOLUTION, ELECTROCHEMICAL DEVICE, LITHIUM ION SECONDARY BATTERY, AND MODULE

TECHNICAL FIELD

The present invention relates to electrolyte solutions, electrochemical devices, lithium ion secondary batteries, and modules.

BACKGROUND ART

Current electric appliances demonstrate a tendency to have a reduced weight and a smaller size, which leads to development of lithium ion secondary batteries having a high energy density. Further, lithium ion secondary batteries are used in more various fields, and thus are desired to have improved characteristics. In particular, the battery characteristics of lithium ion secondary batteries will become more and more important factors when the batteries are put in use for automobiles.

Patent Literature 1 discloses an electrolyte containing a compound represented by formula 1 and a light metal salt represented by formula 2:

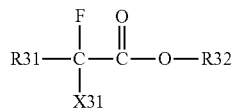

wherein R31 is a hydrogen group, a fluorine group, a C1-C3 alkyl group, or a C1-C3 alkyl group in which one or more hydrogen atoms are replaced by fluorine; X31 is a hydrogen group or a fluorine group; and R32 is a C1 or C2 alkyl group,

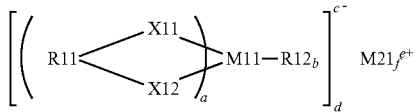

wherein R11 is a —C(=O)—R21-C(=O)— group (where R21 is an alkylene group, a halogenated alkylene group, an arylene group, or a halogenated arylene group) or a —C(=O)—C(=O)— group; R12 is a halogen group, an alkyl group, a halogenated alkyl group, an aryl group, or a halogenated aryl group; X11 and X12 are each oxygen (O) or sulfur (S); M11 is a transition metal element or a 3B group element, 4B group element, or 5B group element in the short-form periodic table; M21 is a 1A group element or 2A group element in the short-form periodic table or aluminium (Al); a is an integer of 1 to 4; b is an integer of 0 to 8; and c, d, e, and f are each an integer of 1 to 3.

Patent Literature 2 discloses a non-aqueous electrolyte solution containing:
an electrolyte salt dissolving solvent (I); and
an electrolyte salt (II),
the solvent (I) containing:
a fluorine-containing ester solvent (A) represented by formula (A) below; and
a fluorine-containing solvent (B) other than the fluorine-containing ester solvent (A):

$$R^1CFXCOOR^2 \qquad (A)$$

wherein $R^1$ is a hydrogen atom, a fluorine atom, or a C1-C3 alkyl group in which hydrogen atoms are optionally replaced by fluorine atoms; X is a hydrogen atom or a fluorine atom (when $R^1$ is a fluorine atom or a perfluoroalkyl group, X is a hydrogen atom); and $R^2$ is a C1-C4 alkyl group.

Patent Literature 3 discloses a non-aqueous electrolyte solution for secondary batteries in which an electrolyte lithium salt is contained in a non-aqueous solvent. The non-aqueous solvent contains a fluorinated acyclic carboxylic acid ester represented by formula (1) below and a film-forming compound which is decomposed in the range of +1.0 to 3.0 V based on the equilibrium potential of lithium metal and lithium ion:

$$R1\text{-}CH_2\text{—COO—}R2 \qquad (1)$$

wherein R1 is a hydrogen atom or an alkyl group; R2 is an alkyl group; the sum of the numbers of carbon atoms in R1 and R2 is 3 or less; when R1 is a hydrogen atom, at least one hydrogen atom in R2 is replaced by fluorine; and when R1 is an alkyl group, at least one hydrogen atom in R1 and/or R2 are replaced by fluorine.

CITATION LIST

Patent Literature
Patent Literature 1: JP 2005-317446 A
Patent Literature 2: JP 2008-257988 A
Patent Literature 3: JP 2009-289414 A

SUMMARY OF INVENTION

Technical Problem

Unfortunately, conventional electrolyte solutions undergo degradation during storage, resulting in a low capacity retention compared to that immediately after preparation, causing an increase in gas production. Degradation of conventional electrolyte solutions is particularly noticeable when the electrolyte solutions are stored at high temperatures.

The present invention was made in view of the current situation described above, and aims to provide an electrolyte solution in which a decrease in capacity retention is suppressed and an increase in gas production is suppressed even when stored at high temperatures.

Solution to Problem

The present inventors found that the above object can be successfully achieved when an electrolyte solution contains a fluorinated acyclic ester having a specific structure, a fluorinated carbonate, and a cyclic acid anhydride. The present invention was thus completed.

Specifically, the present invention provides an electrolyte solution including:
a compound (1) represented by formula (1):

$$CF_3CFX^{11}COOR^{11}$$

wherein $X^{11}$ is a hydrogen atom, a fluorine atom, or a C1-C3 alkyl group in which one or more hydrogen atoms are optionally replaced by fluorine atoms; and $R^{11}$ is a C1-C3 alkyl group in which one or more hydrogen atoms are optionally replaced by fluorine atoms;

a fluorinated carbonate; and
a compound (2) represented by formula (2):

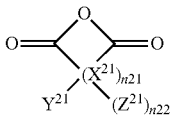

wherein $X^{21}$ is a group at least containing H or C; $n^{21}$ is an integer of 1 to 3; $Y^{21}$ and $Z^{21}$ are the same as or different from each other and are each a group containing at least H, C, O, or F, $n^{22}$ is 0 or 1; and $Y^{21}$ and $Z^{21}$ may be bonded to each other to form a ring.

Preferably, the compound (2) is at least one selected from the group consisting of a compound (3) represented by formula (3):

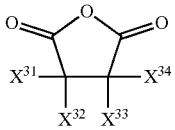

wherein $X^{31}$ to $X^{34}$ are the same as or different from each other and are each a group containing at least H, C, O, or F, and a compound (4) represented by formula (4):

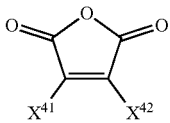

wherein $X^{41}$ and $X^{42}$ are the same as or different from each other and are each a group containing at least H, C, O, or F.

The present invention also relates to an electrochemical device including the electrolyte solution described above.

The present invention also relates to a lithium ion secondary battery including the electrolyte solution described above.

The present invention also relates to a module including the electrochemical device described above or the lithium ion secondary battery described above.

Advantageous Effects of Invention

The present invention provides an electrolyte solution in which a decrease in capacity retention is suppressed and an increase in gas production is suppressed even when stored at high temperatures.

DESCRIPTION OF EMBODIMENTS

The present invention is specifically described below.

The electrolyte solution of the present invention contains a compound (1), a fluorinated carbonate, and a compound (2).

The compound (1) is represented by formula (1):

$CF_3CFX^{11}COOR^{11}$ 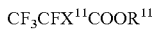

wherein $X^{11}$ is a hydrogen atom, a fluorine atom, or a C1-C3 alkyl group in which hydrogen atoms are optionally replaced by fluorine atoms; and $R^{11}$ is a C1-C3 alkyl group in which hydrogen atoms are optionally replaced by fluorine atoms.

$X^{11}$ is preferably at least one selected from the group consisting of —H, —F, —$CH_3$, —$CHF_2$, —$CH_2F$, and —$CF_3$.

$R^{11}$ is preferably at least one selected from the group consisting of —$CH_3$, —$CH_2CH_3$, —$CF_2H$, —$CFH_2$, —$CF_3$, —$CH_2CF_3$, —$CH_2CF_2H$, —$CH_2CFH_2$, —$CFHCF_3$, —$CFHCF_2H$, —$CFHCFH_2$, —$CF_2CF_3$, —$CF_2CF_2H$, and —$CF_2CFH_2$.

The compound (1) is preferably at least one selected from the group consisting of $CF_3CF_2COOCH_3$, $CF_3CF_2COOC_2H_5$, $CF_3CHFCOOCH_3$, $CF_3CHFCOOC_2H_5$, $CF_3CF(CHF_2)COOCH_3$, $CF_3CF(CHF_2)COOC_2H_5$, $CF_3CF(CH_3)COOCH_3$, $CF_3CF(CH_3)COOC_2H_5$, $CF_3CF(CF_3)COOCH_3$, and $CF_3CF(CF_3)COOC_2H_5$.

The electrolyte solution preferably contains the compound (1) in an amount of 0.0001 to 95% by mass relative to the electrolyte solution in order to further suppress a decrease in capacity retention and an increase in gas production even when stored at high temperatures. The amount of the compound (1) is more preferably 5 to 85% by mass, still more preferably 23.5 to 75% by mass, particularly preferably 24.9 to 75% by mass.

The compound (2) is represented by formula (2):

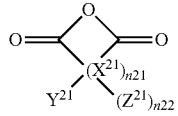

wherein $X^{21}$ is a group at least containing H or C; $n^{21}$ is an integer of 1 to 3; $Y^{21}$ and $Z^{21}$ are the same as or different from each other and are each a group containing at least H, C, O, or F; $n^{22}$ is 0 or 1; and $Y^{21}$ and $Z^{21}$ may be bonded to each other to form a ring.

When $n^{21}$ is 2 or 3, these two or three $X^{21}$'s may be the same as or different from each other.

When there are multiple $Y^{21}$'s and $Z^{21}$'s, these multiple $Y^{21}$'s and multiple $Z^{21}$'s may be the same as or different from each other.

$X^{21}$ is preferably a group represented by —$CY^{21}Z^{21}$— wherein $Y^{21}$ and $Z^{21}$ are as defined above; or a group represented by —$CY^{21}$=$CY^{21}$— wherein $Y^{21}$ and Z are as defined above.

$Y^{21}$ is preferably at least one selected from the group consisting of H—, F—, $CH_3$—, $CH_3CH_2$—, $CH_3CH_2CH_2$—, $CF_3$—, $CF_3CF_2$—, $CH_2FCH_2$—, and $CF_3CF_2CF_2$—.

$Z^{21}$ is preferably at least one selected from the group consisting of H—, F—, $CH_3$—, $CH_3CH_2$—, $CH_3CH_2CH_2$—, $CF_3$—, $CF_3CF_2$—, $CH_2FCH_2$—, and $CF_3CF_2CF_2$—.

Alternatively, $Y^{21}$ and $Z^{21}$ may be bonded to each other to form a carbocyclic ring or a heterocyclic ring which may contain an unsaturated bond and may have aromatic properties. The ring preferably has a carbon number of 3 to 20.

Examples of the compound (2) include glutaric anhydride, citraconic anhydride, glutaconic anhydride, itaconic anhydride, diglycolic anhydride, cyclohexane dicarboxylic anhydride, cyclopentane tetracarboxylic dianhydride, 4-cyclohexene-1,2-dicarboxylic anhydride, 3,4,5,6-tetrahydrophthalic anhydride, 5-norbornene-2,3-dicarboxylic anhydride, phenylsuccinic anhydride, 2-phenylglutaric anhydride, maleic anhydride, methylmaleic anhydride, trifluoromethylmaleic anhydride, phenylmaleic anhydride, succinic anhydride, methylsuccinic anhydride, dimethylsuccinic anhydride, trifluoromethylsuccinic anhydride, monofluorosuccinic anhydride, and tetrafluorosuccinic anhydride.

The compound (2) is preferably at least one selected from the group consisting of a compound (3) represented by formula (3):

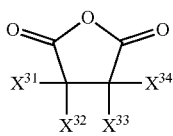

wherein $X^{31}$ to $X^{34}$ are the same as or different from each other and are each a group containing at least H, C, O, or F, and a compound (4) represented by formula (4):

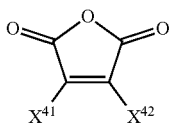

wherein $X^{41}$ and $X^{42}$ are the same as or different from each other and are each a group containing at least H, C, O, or F.

$X^{31}$ to $X^{34}$ are the same as or different from each other and preferably are each at least one selected from the group consisting of alkyl, fluorinated alkyl, alkenyl, and fluorinated alkenyl groups. $X^{31}$ to $X^{34}$ preferably each have a carbon number of 1 to 10, more preferably 1 to 3.

$X^{31}$ to $X^{34}$ are the same as or different from each other and more preferably are each at least one selected from the group consisting of H—, F—, $CH_3$—, $CH_3CH_2$—, $CH_3CH_2CH_2$—, $CF_3$—, $CF_3CF_2$—, $CH_2FCH_2$—, and $CF_3CF_2CF_2$—.

$X^{41}$ and $X^{42}$ are the same as or different from each other and preferably are each at least one selected from the group consisting of alkyl, fluorinated alkyl, alkenyl, and fluorinated alkenyl groups. $X^{41}$ and $X^{42}$ preferably each have a carbon number of 1 to 10, more preferably 1 to 3.

$X^{41}$ and $X^{42}$ are the same as or different from each other and more preferably are each at least one selected from the group consisting of H—, F—, $CH_3$—, $CH_3CH_2$—, $CH_3CH_2CH_2$—, $CF_3$—, $CF_3CF_2$—, $CH_2FCH_2$—, and $CF_3CF_2CF_2$—.

The electrolyte solution preferably contains the compound (2) in an amount of 0.00001 to 15% by mass relative to the electrolyte solution in order to further suppress a decrease in capacity retention and an increase in gas production even when stored at high temperatures. The amount of the compound (2) is more preferably 0.01 to 10% by mass, more preferably 0.1 to 3% by mass, particularly preferably 1.5 to 3% by mass.

The electrolyte solution preferably contains both the compounds (3) and (4) as the compound (2) in order to achieve a high capacity retention and a low gas production. The electrolyte solution is one in which a decrease in capacity retention is suppressed and an increase in gas production is suppressed even when stored at high temperatures. With the presence of both the compounds (3) and (4), the capacity retention can remain high and the gas production can remain low even after storage at high temperatures.

When the electrolyte solution contains both the compounds (3) and (4), even higher capacity retention is achieved and the gas production is further reduced. Thus, the mass ratio of the compound (3) to the compound (4) ((3)/(4)) is preferably 1/99 to 99/1. It is more preferably 20/80 or more, still preferably 40/60 or more, while it is more preferably 98/2 or less, still more preferably 95/5 or less.

When the electrolyte solution contains both the compounds (3) and (4), even higher capacity retention is achieved and the gas production is further reduced. Thus, the electrolyte solution preferably contains the compound (3) and the compound (4) in amounts of 0.08 to 2.50% by mass and 0.02 to 1.50% by mass, respectively, more preferably 0.80 to 2.50% by mass and 0.08 to 1.50% by mass, respectively, relative to the electrolyte solution.

The fluorinated carbonate is preferably at least one selected from the group consisting of fluorinated saturated cyclic carbonates and fluorinated acyclic carbonates.

The electrolyte solution preferably contains the fluorinated carbonate in an amount of 0.0001 to 95% by mass relative to the electrolyte solution in order to further suppress a decrease in capacity retention and an increase in gas production even when stored at high temperatures. The amount of the fluorinated carbonate is more preferably 5 to 85% by mass, still more preferably 23.5 to 75% by mass, particularly preferably 24.9 to 75% by mass.

When the electrolyte solution contains both the fluorinated saturated cyclic carbonate and the fluorinated acyclic carbonate, the ratio of the fluorinated saturated cyclic carbonate to the fluorinated acyclic carbonate (fluorinated saturated cyclic carbonate/fluorinated acyclic carbonate) is preferably 10/90 to 90/10.

The fluorinated saturated cyclic carbonate is a saturated cyclic carbonate with a fluorine atom attached thereto. Specific examples thereof include compounds represented by formula (A) below:

wherein $X^1$ to $X^4$ are the same as or different from each other and are each —H, —CH, —$C_2H_5$, —F, a fluorinated alkyl group optionally having an ether bond, or a fluorinated alkoxy group optionally having an ether bond; at least one of $X^1$ to $X^4$ is –F, a fluorinated alkyl group optionally having an ether bond, or a fluorinated alkoxy group optionally having an ether bond.

If the electrolyte solution of the present invention contains the fluorinated saturated cyclic carbonate and is applied to a lithium ion secondary battery, a stable film can be formed on the negative electrode so that side reactions of the electrolyte solution on the negative electrode may sufficiently be suppressed. As a result, significantly stable, excellent charge and discharge characteristics can be achieved.

The term "ether bond" herein means a bond represented by —O—.

In terms of good permittivity and oxidation resistance, one or two of $X^1$ to $X^4$ is/are preferably a fluorinated alkyl group optionally having —F and/or an ether bond or a fluorinated alkoxy group optionally having an ether bond.

In order to possibly decrease the viscosity at low temperatures, increase the flash point, and improve the solubility of the electrolyte salt, $X^1$ to $X^4$ are preferably individually —H, —F, a fluorinated alkyl group (a), a fluorinated alkyl group (b) having an ether bond, or a fluorinated alkoxy group (c).

The fluorinated alkyl group (a) is an alkyl group in which at least one hydrogen atom is replaced by a fluorine atom. The fluorinated alkyl group (a) preferably has a carbon number of 1 to 20, more preferably 1 to 17, still more preferably 1 to 7, particularly preferably 1 to 5.

If the carbon number is too large, the low-temperature characteristics may be poor and the solubility of the electrolyte salt may be low. If the carbon number is too small, the solubility of the electrolyte salt may be low, the discharge efficiency may be low, and the viscosity may be high, for example.

Examples of the fluorinated alkyl group (a) which has a carbon number of 1 include $CFH_2$—, $CF_2H$—, and $CF_3$—. In particular, $CF_2H$— and $CF_3$— are preferred in terms of high-temperature storage characteristics.

In terms of good solubility of the electrolyte salt, preferred examples of the fluorinated alkyl group (a) having a carbon number of 2 or more include fluorinated alkyl groups represented by formula (a-1) below:

$$R^1\text{-}R^2\text{—} \qquad (a\text{-}1)$$

wherein $R^1$ is a C1 or higher alkyl group optionally having a fluorine atom; $R^2$ is a C1-C3 alkylene group optionally having a fluorine atom; and at least one of R1 and $R^2$ contains a fluorine atom.

$R^1$ and $R^2$ each may further contain an atom other than the carbon atom, hydrogen atom, and fluorine atom.

$R^1$ is a C1 or higher alkyl group optionally having a fluorine atom. R1 is preferably a C1-C16 linear or branched alkyl group. The carbon number of R1 is more preferably 1 to 6, still more preferably 1 to 3.

Specifically, for example, $CH_3$—, $CH_3CH_2$—, $CH_3CH_2CH_2$—, $CH_3CH_2CH_2CH_2$—, and those represented by formulas below:

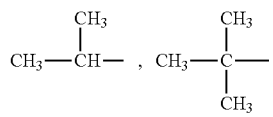

may be mentioned as linear or branched alkyl groups for $R^1$.

When $R^1$ is a linear alkyl group having a fluorine atom, examples thereof include $CF_3$—, $CF_3CH_2$—, $CF_3CF_2$—, $CF_3CH_2CH_2$—, $CF_3CF_2CH_2$—, $CF_3CF_2CF_2$—, $CF_3CH_2CF_2$—, $CF_3CH_2CH_2CH_2$—, $CF_3CF_2CH_2CH_2$—, $CF_3CF_2CF_2CH_2$—, $CF_3CF_2CF_2CF_2$—, $CF_3CF_2CH_2CF_2$—, $CF_3CH_2CH_2CH_2CH_2$—, $CF_3CF_2CH_2CH_2CH_2$—, $CF_3CH_2CF_2CH_2CH_2$—, $CF_3CF_2CF_2CH_2CH_2$—, $CF_3CF_2CF_2CF_2CH_2$—, $CF_3CF_2CH_2CF_2CH_2$—, $CF_3CF_2CH_2CH_2CH_2$—, $CF_3CF_2CH_2CH_2CH_2CH_2$—, $CF_3CF_2CF_2CF_2CH_2CH_2$—, $CF_3CF_2CH_2CH_2CH_2CH_2$—, $HCF_2$—, $HCF_2CH_2$—, $HCF_2CF_2$—, $HCF_2CH_2CH_2$—, $HCF_2CF_2CH_2$—, $HCF_2CH_2CF_2$—, $HCF_2CF_2CH_2CH_2$—, $HCF_2CH_2CF_2CH_2$—, $HCF_2CF_2CF_2CF_2$—, $HCF_2CF_2CH_2CH_2CH_2$—, $HCF_2CH_2CH_2CH_2CH_2$—, $HCF_2CF_2CF_2CF_2CH_2$—, $HCF_2CF_2CF_2CH_2CH_2$—, $FCH_2$—, $FCH_2CH_2$—, $FCH_2CF_2$—, $FCH_2CF_2CH_2$—, $FCH_2CF_2CF_2$—, $CH_3CF_2CH_2$—, $CH_3CF_2$—, $CH_3CF_2CH_2CF_2$—, $CH_3CF_2CF_2CF_2$—, $CH_3CF_2CF_2$—, $CH_3CF_2CH_2CH_2$—, $CH_3CF_2CF_2CF_2$—, $CH_3CF_2CF_2CH_2CH_2$—, $CH_3CF_2CF_2CF_2CH_2$—, $CH_3CH_2CF_2CF_2CH_2$—, $CH_3CF_2CH_2CF_2CH_2CH_2$—, $CH_3CF_2CH_2CF_2CH_2CH_2$—, $HCFClCF_2CH_2$—, $HCF_2CFClCH_2$—, $HCF_2CFClCF_2CFClCH_2$—, and $HCFClCF_2CFClCF_2CH_2$—.

When $R^1$ is a branched alkyl group having a fluorine atom, those shown below:

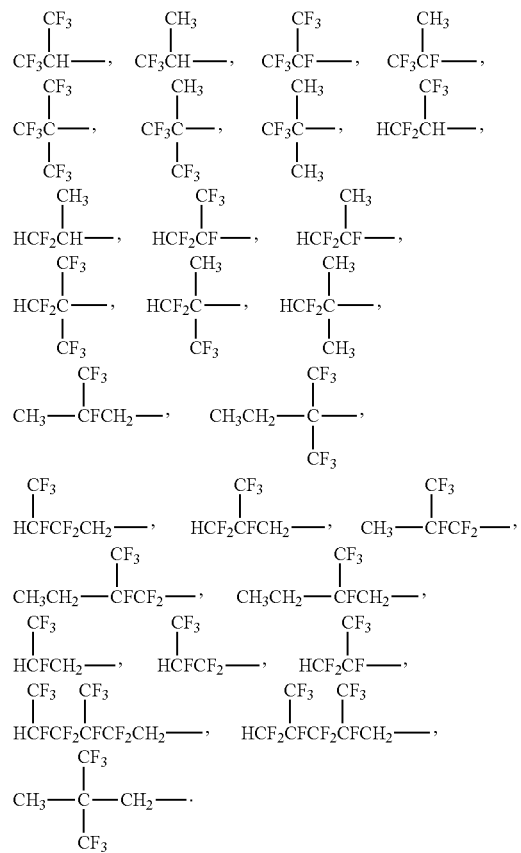

may be preferably mentioned. When the group has a branch represented by —$CH_3$ or —$CF_3$, for example, the viscosity is likely to be high. Thus, the number of such branches is more preferably small (one) or zero.

$R^2$ is a C1-C3 alkylene group optionally having a fluorine atom. $R^2$ may be a linear or branched group. Examples of a minimum structural unit constituting such a linear or branched alkylene group are shown below. $R^2$ is formed by one or combination of these units.

(i) Linear minimum structural units:

—$CH_2$—, —CHF—, —$CF_2$—, —CHCl—, —CFCl—, —$CCl_2$—

(ii) Branched minimum structural units:

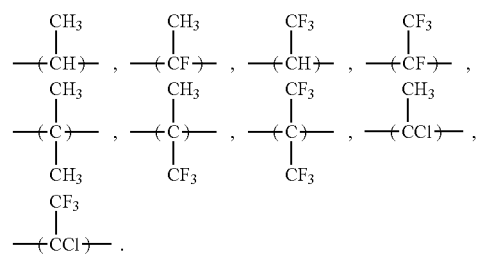

Preferred among these exemplified units are Cl-free structural units because such units are not dehydrochlorinated by a base, and thus are more stable.

When $R^2$ is a linear group, the group preferably consists of the above linear minimum structural unit, preferably —$CH_2$—, —$CH_2CH_2$—, or —$CF_2$—. In order to further improve the solubility of the electrolyte salt, —$CH_2$— or —$CH_2CH_2$— is more preferred.

When $R^2$ is a branched group, the group includes at least one of the above branched minimum structural units.

Preferred examples thereof include those represented by a formula: —$(CX^aX^b)$— wherein $X^a$ is H, F, $CH_3$, or $CF_3$; $X^b$ is $CH_3$ or $CF_3$; and when $X^b$ is $CF_3$, $X^a$ is H or $CH_3$. Such groups can further improve the solubility of the electrolyte salt.

For example, $CF_3CF_2$—, $HCF_2CF_2$—, $H_2CFCF_2$—, $CH_3CF_2$—, $CF_3CHF$—, $CF_3CF_2CF_2$—, $HCF_2CF_2CF_2$—, $H_2CFCF_2CF_2$—, $CH_3CF_2CF_2$—, and those shown below:

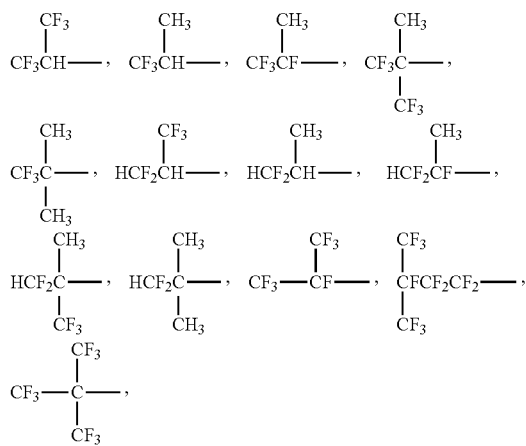

may be mentioned as preferred examples of the fluorinated alkyl group (a).

The fluorinated alkyl group (b) having an ether bond is an alkyl group having an ether bond in which at least one hydrogen atom is replaced by a fluorine atom. The fluorinated alkyl group (b) having an ether bond preferably has a carbon number of 2 to 17. If the carbon number is too large, the fluorinated saturated cyclic carbonate may have a high viscosity, and also the number of fluorine-containing groups increases. Thus, the solubility of the electrolyte salt may be poor due to a reduction in the permittivity, and the compatibility with other solvents may be poor. Accordingly, the carbon number of the fluorinated alkyl group (b) having an ether bond is preferably 2 to 10, more preferably 2 to 7.

The alkylene group constituting the ether moiety of the fluorinated alkyl group (b) having an ether bond may be a linear or branched alkylene group. Examples of a minimum structural unit constituting such a linear or branched alkylene group are shown below.
(i) Linear minimum structural units:
—$CH_2$—, —CHF—, —$CF_2$—, —CHCl—, —CFCl—, —$CCl_2$—
(ii) Branched minimum structural units:

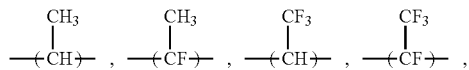

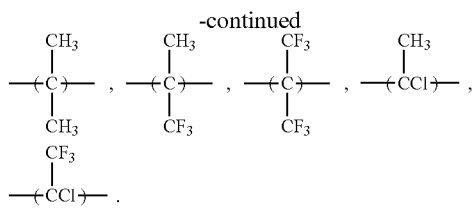

The alkylene group may be formed by one of these minimum structural units alone, or may be formed by a combination of linear units (i), of branched units (ii), or of a linear unit (i) and a branched unit (ii). Preferred examples will be mentioned in detail later.

Preferred among these exemplified units are Cl-free structural units because such units are not dehydrochlorinated by a base, and thus are more stable.

Still more preferred examples of the fluorinated alkyl group (b) having an ether bond include those represented by formula (b-1) below:

$$R^3—(OR^4)_{n1}—\qquad(b\text{-}1)$$

wherein $R^3$ is preferably a C1-C6 alkyl group optionally having a fluorine atom; $R^4$ is preferably a C1-C4 alkylene group optionally having a fluorine atom; n1 is an integer of 1 to 3; and at least one of $R^3$ and $R^4$ contains a fluorine atom.

Examples of the groups for $R^3$ and $R^4$ include the following, and any appropriate combination of these groups can provide the fluorinated alkyl group (b) having an ether bond represented by formula (b-1). Still, the groups are not limited thereto.

(1) $R^3$ is preferably an alkyl group represented by a formula: $X^c_3C—(R^5)_{n2}$—, where three $X^c$'s are the same as or different from each other and are each H or F; $R^5$ is a C1-C5 alkylene group optionally having a fluorine atom; and n2 is 0 or 1.

When n2 is 0, $R^3$ may be $CH_3$—, $CF_3$—, $HCF_2$—, or $H_2CF$—, for example.

When n2 is 1, specific examples of a linear group for $R^3$ include $CF_3CH_2$—, $CF_3CF_2$—, $CF_3CH_2CH_2$—, $CF_3CF_2CH_2$—, $CF_3CF_2CF_2$—, $CF_3CH_2CF_2$—, $CF_3CH_2CH_2CH_2$—, $CF_3CF_2CH_2CH_2$—, $CF_3CH_2CF_2CH_2$—, $CF_3CF_2CF_2CH_2$—, $CF_3CF_2CF_2CF_2$—, $CF_3CF_2CH_2CF_2$—, $CF_3CH_2CH_2CH_2CH_2$—, $CF_3CF_2CH_2CH_2CH_2$—, $CF_3CH_2CF_2CH_2CH_2$—, $CF_3CF_2CF_2CH_2CH_2$—, $CF_3CF_2CF_2CH_2$—, $CF_3CF_2CH_2CF_2CH_2$—, $CF_3CF_2CF_2CH_2CH_2CH_2$—, $CF_3CF_2CH_2CF_2CH_2CH_2$—, $HCF_2CH_2$—, $HCF_2CF_2$—, $HCF_2CH_2CH_2$—, $HCF_2CF_2CH_2$—, $HCF_2CH_2CF_2$—, $HCF_2CF_2CH_2CH_2$—, $HCF_2CH_2CF_2CH_2$—, $HCF_2CF_2CF_2$—, $HCF_2CF_2CH_2CH_2CH_2$—, $HCF_2CH_2CF_2CH_2CH_2$—, $HCF_2CF_2CF_2CF_2CH_2$—, $HCF_2CF_2CF_2CH_2CH_2$—, $FCH_2CH_2$—, $FCH_2CF_2$—, $FCH_2CF_2CH_2$—, $CH_3CF_2$—, $CH_3CH_2$—, $CH_3CF_2CH_2$—, $CH_3CF_2CF_2$—, $CH_3CH_2CH_2$—, $CH_3CF_2CH_2CF_2$—, $CH_3CF_2CF_2CF_2$—, $CH_3CH_2CF_2CF_2$—, $CH_3CH_2CH_2CH_2$—, $CH_3CF_2CH_2CF_2CH_2$—, $CH_3CF_2CF_2CH_2$—, $CH_3CF_2CF_2CH_2CH_2$—, $CH_3CH_2CF_2CF_2CH_2$—, $CH_3CF_2CH_2CF_2CH_2CH_2$—, $CH_3CH_2CF_2CF_2CH_2CH_2$—, and $CH_3CF_2CH_2CF_2CH_2CH_2$—.

When n2 is 1, those shown below:

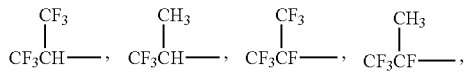

-continued

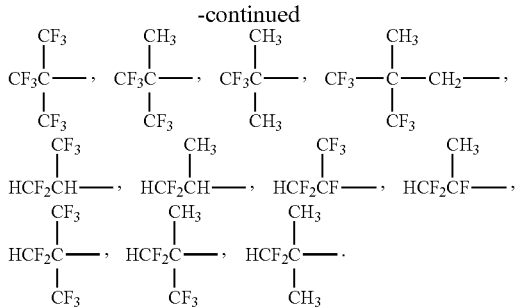

may be mentioned as branched groups for $R^3$.

When the group for $R^3$ has a branch such as $CH_3$— or $CF_3$—, the viscosity is likely to be high. Thus, the group for $R^3$ is more preferably a linear group.

(2) In —$(OR^4)_{n1}$— of formula (b-1), n1 is an integer of 1 to 3, preferably 1 or 2. When n1 is 2 or 3, $R^4$'s may be the same as or different from each other.

Preferred specific examples of the group for $R^4$ include the following linear or branched groups.

Examples of the linear groups include —$CH_2$—, —CHF—, —$CF_2$—, —$CH_2CH_2$—, —$CF_2CH_2$—, —$CF_2CF_2$—, —$CH_2CF_2$—, —$CH_2CH_2CH_2$—, —$CH_2CH_2CF_2$—, —$CH_2CF_2CH_2$—, —$CH_2CF_2CF_2$—, —$CF_2CH_2CH_2$—, —$CF_2CF_2CH_2$—, —$CF_2CH_2CF_2$—, and —$CF_2CF_2CF_2$—.

Those shown below:

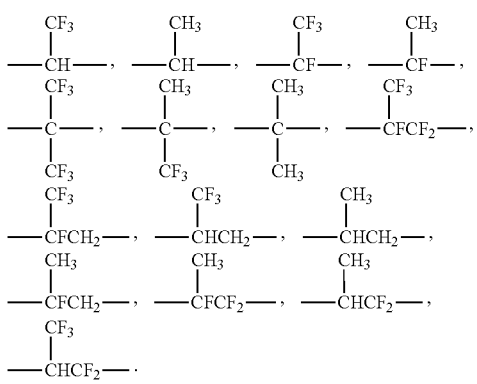

may be mentioned as branched groups.

The fluorinated alkoxy group (c) is an alkoxy group in which at least one hydrogen atom is replaced by a fluorine atom. The fluorinated alkoxy group (c) preferably has a carbon number of 1 to 17. The carbon number is more preferably 1 to 6.

The fluorinated alkoxy group (c) is particularly preferably a fluorinated alkoxy group represented by a formula: $X^d{}_3C$—$(R^6)_{n3}$—O— wherein three $X^d$'s are the same as or different from each other and are each H or F; $R^6$ is preferably a C1-C5 alkylene group optionally having a fluorine atom; n3 is 0 or 1; and any of the three $X^d$'s contains a fluorine atom.

Specific examples of the fluorinated alkoxy group (c) include fluorinated alkoxy groups in which an oxygen atom is bonded to an end of the alkyl group for R1 in formula (a-1).

The fluorinated alkyl group (a), the fluorinated alkyl group (b) having an ether bond, and the fluorinated alkoxy group (c) in the fluorinated saturated cyclic carbonate each preferably have a fluorine content of 5% by mass or more. If the fluorine content is too low, effects of decreasing the viscosity at low temperatures and increasing the flash point may not be sufficiently achieved. From this viewpoint, the fluorine content is more preferably 10% by mass or more, still more preferably 12% by mass or more. The upper limit thereof is usually 76% by mass.

The fluorine content of each of the fluorinated alkyl group (a), the fluorinated alkyl group (b) having an ether bond, and the fluorinated alkoxy group (c) is a value calculated based on the corresponding structural formula by the following formula:

{(Number of fluorine atoms×19)/(Formula weight of each group)}×100(%).

In terms of good permittivity and oxidation resistance, the fluorine content in the whole fluorinated saturated cyclic carbonate is preferably 10% by mass or more, more preferably 15% by mass or more. The upper limit thereof is usually 76% by mass.

The fluorine content in the whole fluorinated saturated cyclic carbonate is a value calculated based on the structural formula of the fluorinated saturated cyclic carbonate by the following formula:

{(Number of fluorine atoms×19)/(Molecular weight of fluorinated saturated cyclic carbonate)}×100 (%).

Specific examples of the fluorinated saturated cyclic carbonate include the following.

Those shown below:

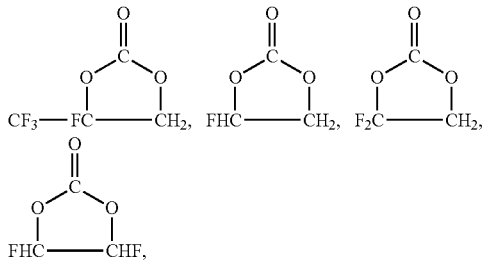

may be mentioned as specific examples of the fluorinated saturated cyclic carbonate in which at least one of $X^1$ to $X^4$ is —F. These compounds have a high withstand voltage and give a good solubility of the electrolyte salt.

Alternatively, those shown below:

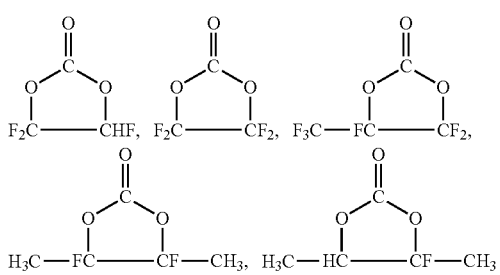

may also be used.

Those shown below:
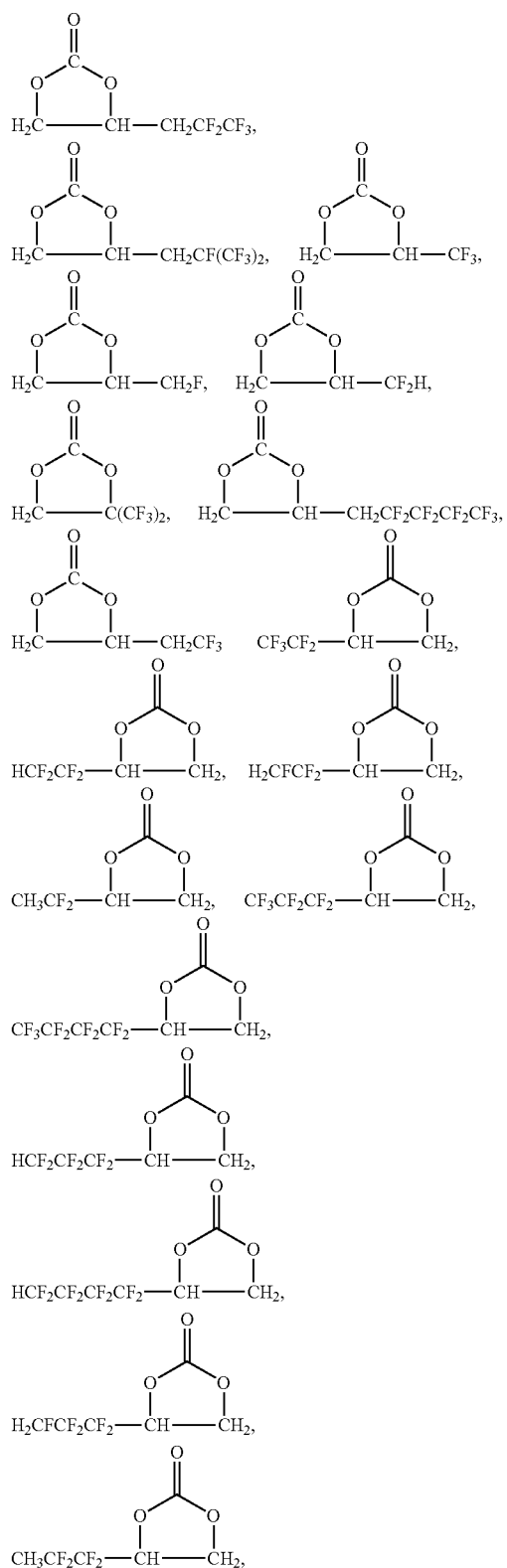
Those shown below:
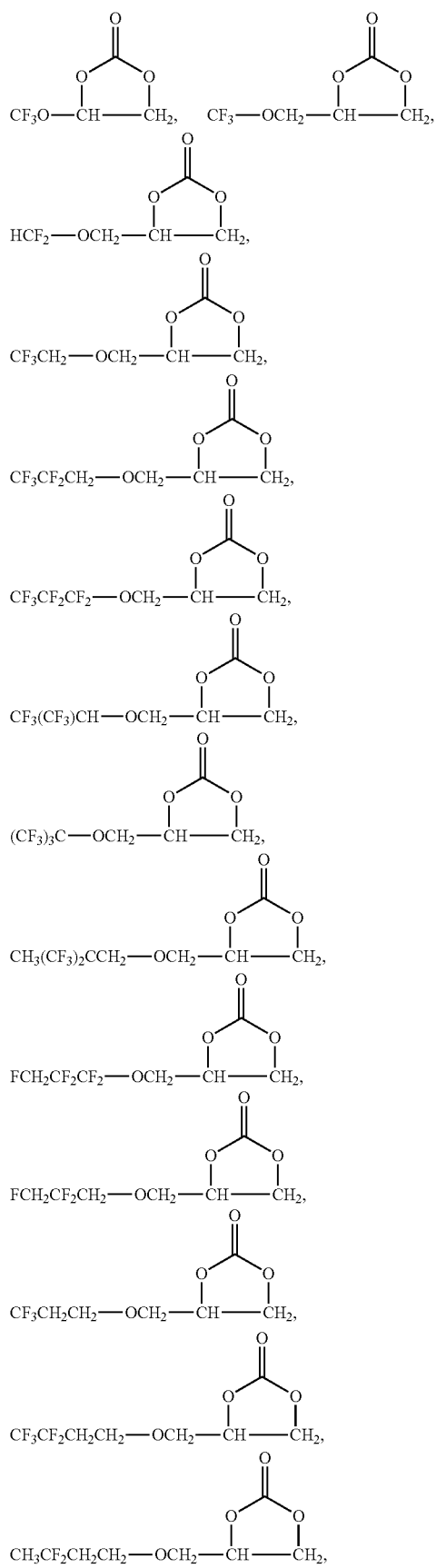
may be mentioned as specific examples of the fluorinated saturated cyclic carbonate in which at least one of $X^1$ to $X^4$ is a fluorinated alkyl group (a) and the others thereof are —H.

-continued
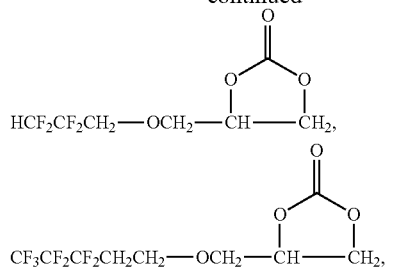
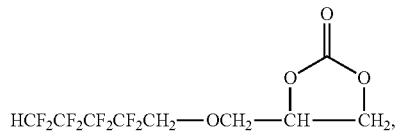
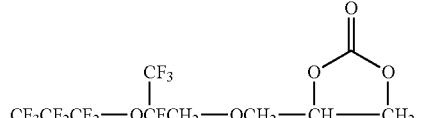
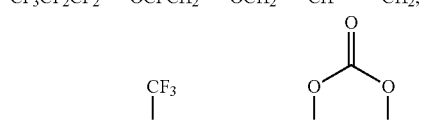
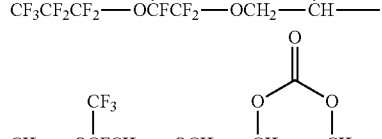
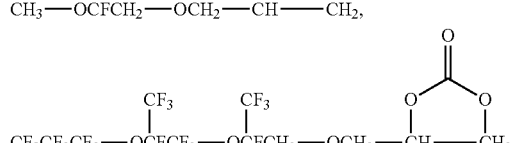
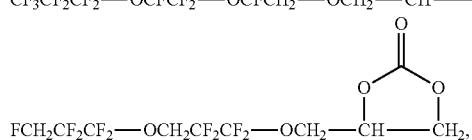
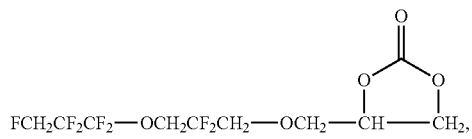
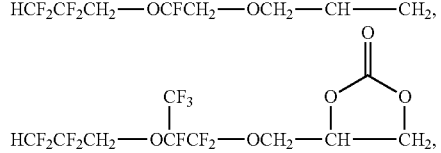
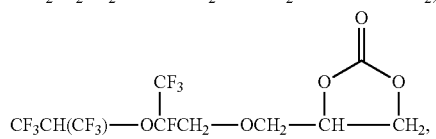
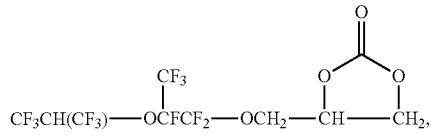
-continued
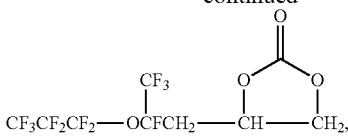
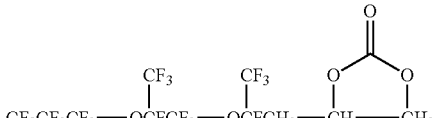
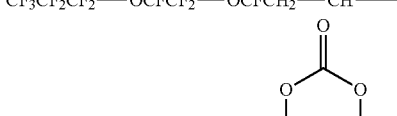
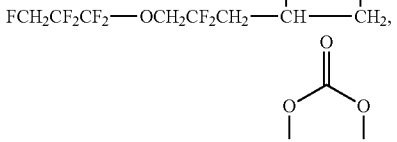
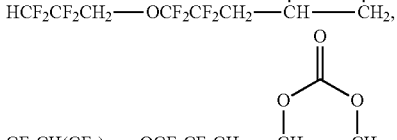
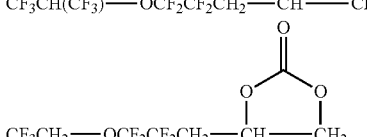
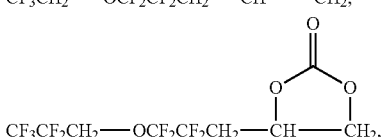
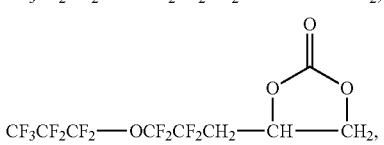
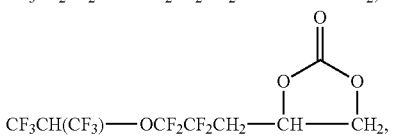
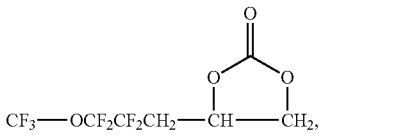
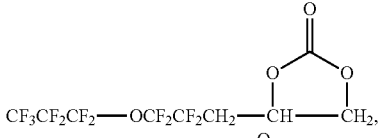
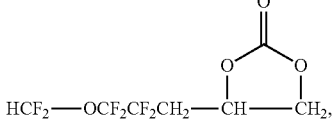
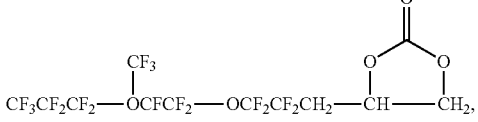

-continued

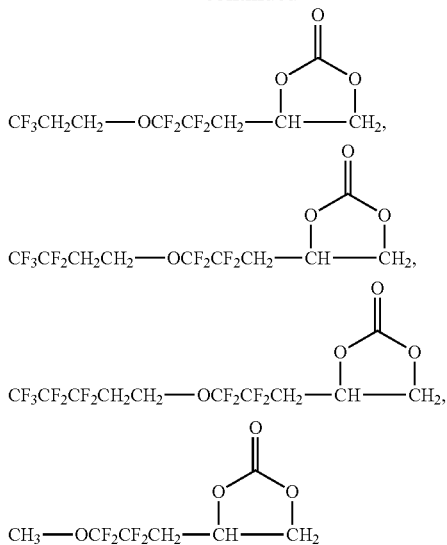

may be mentioned as specific examples of the fluorinated saturated cyclic carbonate in which at least one of $X^1$ to $X^4$ is a fluorinated alkyl group (b) having an ether bond or a fluorinated alkoxy group (c) and the others thereof are —H.

In particular, the fluorinated saturated cyclic carbonate is preferably any one of the following compounds.

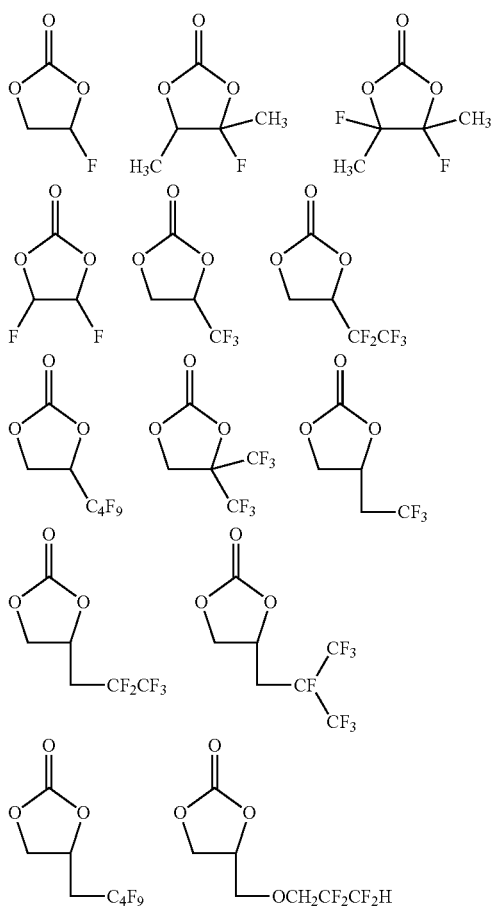

The fluorinated saturated cyclic carbonate is not limited to the above specific examples. The above examples of the fluorinated saturated cyclic carbonate may be used alone, or two or more thereof may be used in any combination at any ratio.

Examples of the fluorinated acyclic carbonate include compounds represented by formula (B):

$$Rf^1OCOOR^7 \quad (B)$$

wherein $Rf^1$ is a C1-C7 fluorinated alkyl group; and $R^7$ is an alkyl group optionally having a C1-C7 fluorine atom.

$Rf^1$ is a C1-C7 fluorinated alkyl group; and $R^7$ is a C1-C7 alkyl group optionally having a fluorine atom.

The fluorinated alkyl group is an alkyl group in which at least one hydrogen atom is replaced by a fluorine atom. When $R^7$ is an alkyl group containing a fluorine atom, it is a fluorinated alkyl group.

$Rf^1$ and $R^7$ each preferably have a carbon number of 2 to 7, more preferably 2 to 4, in terms of low viscosity.

If the carbon number is too large, it may result in poor low-temperature characteristics or a low solubility of the electrolyte salt. If the carbon number is too small, it may result in, for example, a low solubility of the electrolyte salt, a low discharge efficiency, and a high viscosity.

Examples of the C1 or higher fluorinated alkyl group include $CFH_2$—, $CF_2H$—, and $CF_3$—. In particular, $CF_2H$— or $CF_3$— is preferred in terms of high-temperature storage characteristics.

In terms of good solubility of the electrolyte salt, preferred examples of the fluorinated alkyl group having a carbon number of 2 or more include a fluorinated alkyl group represented by formula (d-1) below:

$$R1-R^2— \quad (d-1)$$

wherein R1 is a C1 or higher alkyl group optionally having a fluorine atom; $R^2$ is a C1-C3 alkylene group optionally having a fluorine atom; and at least one of R1 and $R^2$ contains a fluorine atom.

$R^1$ and $R^2$ each may further contain an atom other than the carbon atom, hydrogen atom, and fluorine atom.

$R^1$ is a C1 or higher alkyl group optionally having a fluorine atom. $R^1$ is preferably a C1-C6 linear or branched alkyl group. The carbon number of $R^1$ is more preferably 1 to 6, still more preferably 1 to 3.

Specifically, for example, $CH_3$—, $CH_3CH_2$—, $CH_3CH_2CH_2$—, $CH_3CH_2CH_2CH_2$—, and the groups represented by formulas below:

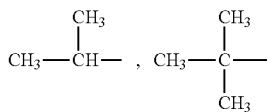

may be mentioned as linear or branched alkyl groups for $R^1$.

When $R^1$ is a linear alkyl group having a fluorine atom, examples thereof include $CF_3$—, $CF_3CH_2$—, $CF_3CF_2$—, $CF_3CH_2CH_2$—, $CF_3CF_2CH_2$—, $CF_3CF_2CF_2$—, $CF_3CH_2CF_2$—, $CF_3CH_2CH_2CH_2$—, $CF_3CF_2CH_2CH_2$—, $CF_3CH_2CF_2CH_2$—, $CF_3CF_2CF_2CH_2$—, $CF_3CF_2CF_2CF_2$—, $CF_3CF_2CH_2CF_2$—, $CF_3CH_2CH_2CH_2CH_2$—, $CF_3CF_2CH_2CH_2CH_2$—, $CF_3CH_2CF_2CH_2CH_2$—, $CF_3CF_2CF_2CH_2CH_2$—, $CF_3CF_2CF_2CF_2CH_2$—, $CF_3CF_2CH_2CF_2CH_2$—, $CF_3CF_2CH_2CH_2CH_2CH_2$—, $CF_3CF_2CF_2CF_2CH_2CH_2$—, $CF_3CH_2CF_2CH_2CH_2CH_2$—, $HCF_2$—, $HCF_2CH_2$—, $HCF_2CF_2$—, $HCF_2CH_2CH_2$—, $HCF_2CF_2CH_2$—, $HCF_2CH_2CF_2$—, $HCF_2CF_2CH_2CH_2$—, $HCF_2CH_2CF_2CH_2$—, $HCF_2CF_2CF_2CF_2$—, $HCF_2CF_2CH_2CH_2CH_2$—, $HCF_2CH_2CF_2CH_2CH_2$—, $HCF_2CF_2CF_2CF_2CH_2$—, $HCF_2CF_2CF_2CF_2CH_2CH_2$—, $FCH_2$—, $FCH_2CH_2$—, $FCH_2CF_2$—, $FCH_2CF_2CH_2$—, $FCH_2CF_2CF_2$—, $CH_3CF_2CH_2$—, $CH_3CF_2CF_2$—, $CH_3CF_2CH_2CF_2$—, $CH_3CF_2CF_2CF_2$—, $CH_3CH_2CF_2CF_2$—, $CH_3CF_2CH_2CF_2CH_2$—, $CH_3CF_2CF_2CF_2CH_2$—, $CH_3CF_2CF_2CH_2CH_2$—, $CH_3CH_2CF_2CF_2CH_2$—, $CH_3CF_2CH_2CF_2CH_2CH_2$—, $CH_3CF_2CH_2CF_2CH_2CH_2$—, $HCFClCF_2CH_2$—, $HCF_2CFClCH_2$—, $HCF_2CFClCF_2CFClCH_2$—, and $HCFClCF_2CFClCF_2CH_2$—.

When $R^1$ is a branched alkyl group having a fluorine atom, those shown below may be preferably mentioned:

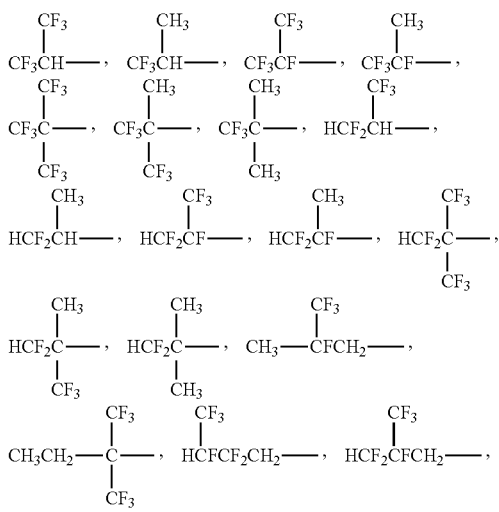

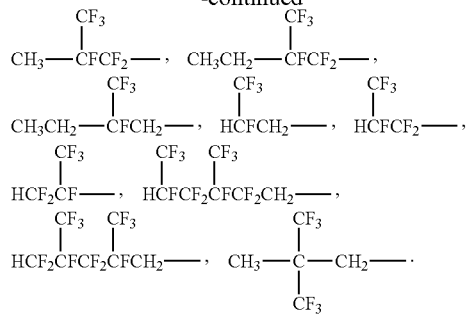

When the group has a branch represented by —$CH_3$ or —$CF_3$, for example, the viscosity is likely to be high. Thus, the number of such branches is more preferably small (one) or zero.

$R^2$ is a C1-C3 alkylene group optionally having a fluorine atom. $R^2$ may be a linear or branched group. Examples of a minimum structural unit constituting such a linear or branched alkylene group are shown below. $R^2$ is formed by one or combination of these units.

(i) Linear minimum structural units:
—$CH_2$—, —$CHF$—, —$CF_2$—, —$CHCl$—, —$CFCl$—, —$CCl_2$—

(ii) Branched minimum structural units:

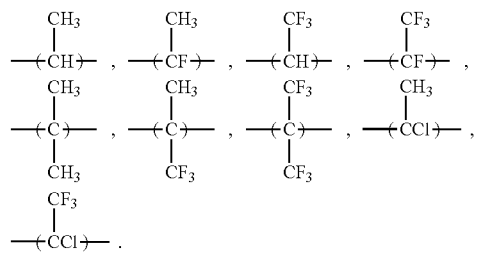

Preferred among these exemplified units are Cl-free structural units because such units are not dehydrochlorinated by a base, and thus are more stable.

When $R^2$ is a linear group, the group consists of the above linear minimum structural unit, preferably —$CH_2$—, —$CH_2CH_2$—, or —$CF_2$—. For further improving the solubility of the electrolyte salt, —$CH_2$— or —$CH_2CH_2$— is more preferred.

When $R^2$ is a branched group, the group includes at least one of the above branched minimum structural units. Preferred examples thereof include those represented by a formula: —$(CX^aX^b)$— wherein $X^a$ is H, F, $CH_3$, or $CF_3$; $X^b$ is $CH_3$ or $CF_3$; and when $X^b$ is $CF_3$, $X^a$ is H or $CH_3$. Such groups can further improve the solubility of the electrolyte salt.

Specifically, for example, $CF_3CF_2$—, $HCF_2CF_2$—, $H_2CFCF_2$—, $CH_3CF_2$—, $CF_3CF_2CF_2$—, $HCF_2CF_2CF_2$—, $H_2CFCF_2CF_2$—, $CH_3CF_2CF_2$—, and those shown below:

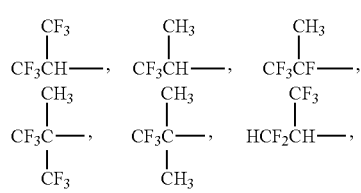

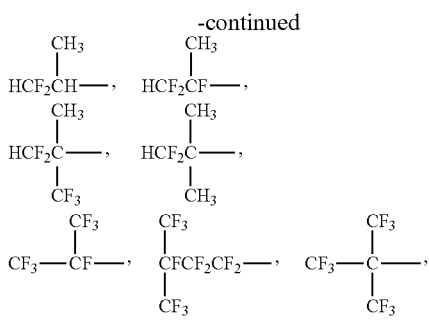

may be mentioned as preferred fluorinated alkyl groups.

In particular, $CF_3-$, $CF_3CF_2-$, $(CF_3)_2CH-$, $CF_3CH_2-$, $C_2F_5CH_2-$, $CF_3CF_2CH_2-$, $HCF_2CF_2CH_2-$, and $CF_3CFHCF_2CH_2-$ are preferred as the fluorinated alkyl group in $Rf^1$ and $R^7$. More preferred are $CF_3CH_2-$, $CF_3CF_2CH_2-$, and $HCF_2CF_2CH_2-$ in terms of high flame retardancy, good rate characteristics, and good oxidation resistance.

When $R^7$ is an alkyl group free of fluorine atoms, it is a C1-C7 alkyl group. $R^7$ preferably has a carbon number of 1 to 4, more preferably 1 to 3, in terms of low viscosity.

Examples of the alkyl group free of fluorine atoms include $CH_3-$, $CH_3CH_2-$, $(CH_3)_2CH-$, and $C_3H_7-$. In particular, $CH_3-$ and $CH_3CH_2-$ are preferred in terms of low viscosity and good rate characteristics.

The fluorinated acyclic carbonate preferably has a fluorine content of 20 to 70% by mass. When the fluorine content is in the above range, the compatibility with the solvent and the solubility of the salt can be maintained. The fluorine content is more preferably 30% by mass or more, still more preferably 35% by mass or more, while it is more preferably 60% by mass or less, still more preferably 50% by mass or less.

In the present invention, the fluorine content is a value calculated based on the structural formula of the fluorinated acyclic carbonate by the following formula:

{(Number of fluorine atoms×19)/(Molecular weight of fluorinated acyclic carbonate)}×100(%).

The fluorinated acyclic carbonate is preferably any of the following compounds in terms of low viscosity.

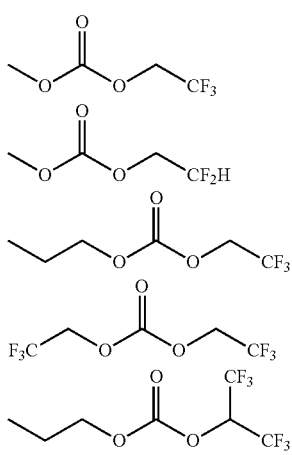

Preferably, the electrolyte solution contains
the compound (1) in an amount of 0.0001 to 95% by mass,
the fluorinated carbonate in an amount of 0.0001 to 95% by mass, and
the compound (2) in an amount of 0.00001 to 15% by mass, relative to the electrolyte solution.

More preferably, the electrolyte solution contains
the compound (1) in an amount of 5 to 85% by mass,
the fluorinated carbonate in an amount of 5 to 85% by mass, and
the compound (2) in an amount of 0.01 to 10% by mass, relative to the electrolyte solution.

Still more preferably, the electrolyte solution contains
the compound (1) in an amount of 24.9 to 75% by mass,
the fluorinated carbonate in an amount of 24.9 to 75% by mass, and
the compound (2) in an amount of 0.1 to 3% by mass, relative to the electrolyte solution.

Most preferably, the electrolyte solution contains
the compound (1) in an amount of 23.5 to 75% by mass,
the fluorinated carbonate in an amount of 23.5 to 75% by mass, and
the compound (2) in an amount of 1.5 to 3% by mass, relative to the electrolyte solution.

The electrolyte solution can further contain a non-fluorinated carbonate. Examples of the non-fluorinated carbonate include non-fluorinated saturated cyclic carbonates and non-fluorinated acyclic carbonates.

Examples of the non-fluorinated saturated cyclic carbonates include ethylene carbonate (EC), propylene carbonate (PC), and butylene carbonate.

In order to achieve a high permittivity and a suitable viscosity, the non-fluorinated saturated cyclic carbonate is preferably at least one compound selected from the group consisting of ethylene carbonate, propylene carbonate, and butylene carbonate.

The non-fluorinated saturated cyclic carbonate may include one of the above compounds or may include two or more thereof in combination.

Examples of the non-fluorinated acyclic carbonate include hydrocarbon acyclic carbonates such as $CH_3OCOOCH_3$ (dimethyl carbonate: DMC), $CH_3CH_2OCOOCH_2CH_3$ (diethyl carbonate: DEC), $CH_3CH_2OCOOCH_3$ (ethyl methyl carbonate: EMC), $CH_3OCOOCH_2CH_2CH_3$ (methyl propyl carbonate), methyl butyl carbonate, ethyl propyl carbonate, and ethyl butyl carbonate. In particular, the non-fluorinated acyclic carbonate is preferably at least one selected from the group consisting of ethyl methyl carbonate, diethyl carbonate, and dimethyl carbonate.

The amount of the non-fluorinated acyclic carbonate is preferably 25% by mass or less, more preferably 10% by mass or less, relative to the electrolyte solution, to avoid impairing the performance of the electrolyte solution. The lower limit may be 0% by mass.

The electrolyte solution of the present invention may contain a borate.

Examples of the borate include compounds represented by formula (5) below:

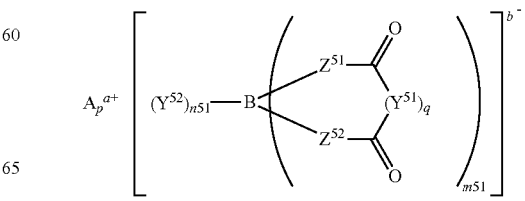

wherein $A^{a+}$ is a metal ion, a hydrogen ion, or an onium ion; a is an integer of 1 to 3; b is an integer of 1 to 3; p is b/a; $m^{51}$ is an integer of 1 or 2; $n^{51}$ is an integer of 0 to 8; q is 0 or 1; and $Y^{51}$ is a C1-C10 alkylene group, a C1-C10 halogenated alkylene group, a C6-C20 arylene group, or a C6-C20 halogenated arylene group (the alkylene group, the halogenated alkylene group, the arylene group, and the halogenated arylene group each may have a substituent or a hetero atom in the structure; and $m^{51}$ number of $Y^{51}$'s may be bonded to each other when q is 1 and $m^{51}$ is 2). $Y^{52}$ is a halogen atom, a C1-C10 alkyl group, a C1-C10 halogenated alkyl group, a C6-C20 aryl group, a C6-C20 halogenated aryl group (the alkylene group, the halogenated alkylene group, the arylene group, and the halogenated arylene group each may have a substituent or a hetero atom in the structure; and $n^{51}$ number of $Y^{52}$'s may be bonded to each other to form a ring when $n^{51}$ is 2 to 8), or $-Z^3Y^{53}$. $Z^{51}$, $Z^{52}$, and $Z^{53}$ are each individually O, S, or $NY^{54}$. $Y^{53}$ and $Y^{54}$ are each individually a hydrogen atom, a C1-C10 alkyl group, a C1-C10 halogenated alkyl group, a C6-C20 aryl group, or a C6-C20 halogenated aryl group (the alkylene group, the halogenated alkylene group, the arylene group, and the halogenated arylene group each may have a substituent or a hetero atom in the structure; and when there are multiple $Y^{53}$'s or $Y^{54}$'s, each of these may be bonded to each other to form a ring).

In formula (5), $A^{a+}$ is a metal ion, a hydrogen ion, or an onium ion.

Examples of $A^{a+}$ include a lithium ion, a sodium ion, a potassium ion, a magnesium ion, a calcium ion, a barium ion, a caesium ion, a silver ion, a zinc ion, a copper ion, a cobalt ion, an iron ion, a nickel ion, a manganese ion, a titanium ion, a lead ion, a chromium ion, a vanadium ion, a ruthenium ion, an yttrium ion, lanthanoid ions, actinoid ions, a tetrabutyl ammonium ion, a tetraethyl ammonium ion, a tetramethyl ammonium ion, a triethyl methyl ammonium ion, a triethyl ammonium ion, a pyridinium ion, an imidazolium ion, a hydrogen ion, a tetraethyl phosphonium ion, a tetramethyl phosphonium ion, a tetraphenyl phosphonium ion, a triphenyl sulfonium ion, and a triethyl sulfonium ion.

In applications such as electrochemical devices, $A^{a+}$ is preferably a lithium ion, a sodium ion, a magnesium ion, a tetraalkyl ammonium ion, or a hydrogen ion, particularly preferably a lithium ion. In other words, the borate in the present invention is preferably a lithium borate. The valence (a) of the cation $A^{a+}$ is an integer of 1 to 3. If the valence is greater than 3, the crystal lattice energy is high and the borate has difficulty in dissolving in the solvent. Thus, the valence is more preferably 1 if good solubility is needed. The valence (b) of the anion is also an integer of 1 to 3, particularly preferably 1. The constant p that represents the ratio between the cation and the anion is naturally defined by the ratio b/a between the valences thereof.

Next, the ligands in the compound represented by formula (5) are described. As used herein, organic or inorganic groups bonded to the boron atom in formula (5) are referred to as ligands.

$Y^{51}$ in formula (5) is a C1-C10 alkylene group, a C1-C10 halogenated alkylene group, a C6-C20 arylene group, or a C6-C20 halogenated arylene group. These alkylene groups and arylene groups each may have a substituent or a hetero atom in the structure. Specifically, instead of the hydrogen of the alkylene group or the arylene group, the structure may have a halogen atom, an acylic or cyclic alkyl group, an aryl group, an alkenyl group, an alkoxy group, an aryloxy group, a sulfonyl group, an amino group, a cyano group, a carbonyl group, an acyl group, an amide group, or a hydroxy group as a substituent; or, instead of the carbon of the alkylene or the arylene, the structure may have nitrogen, sulfur, or oxygen introduced therein. When q is 1 and $m^{51}$ is 2, $m^{51}$ number of $Y^{51}$'s may be bonded to each other. One such example is a ligand such as ethylenediamine tetraacetic acid.

$Y^{52}$ is a halogen atom, a C1-C10 alkyl group, a C1-C10 halogenated alkyl group, a C6-C20 aryl group, a C6-C20 halogenated aryl group, or $-Z^{53}Y^{53}$ ($Z^{53}$ and $Y^{53}$ will be described later). Similar to $Y^{51}$, the alkyl groups and the aryl groups each may have a substituent or a hetero atom in the structure, and when $n^{51}$ is 2 to 8, $n^{51}$ number of $Y^{52}$'s may be bonded to each other to form a ring. $Y^{52}$ is preferably an electron withdrawing group, particularly preferably a fluorine atom. This is because a fluorine atom can improve the solubility and the degree of dissociation of an anion compound salt, which involves improvement of the ion conductivity. This is also because a fluorine atom can improve the oxidation resistance, which makes it possible to restrain occurrence of side reactions.

$Z^{51}$, $Z^{52}$, and $Z^{53}$ are each individually O, S, or $NY^{54}$. The ligands are bonded to the boron atom via these hetero atoms. Bonding with an atom other than O, S, and $NY^{54}$ may also be possible, but is very complicated in terms of synthesis. $Z^{51}$ and $Z^{52}$ are each preferably O. The compound represented by formula (5) characteristically has bonds to the boron atom via $Z^{51}$ and $Z^{52}$ in the same ligand. Such a ligand forms a chelate structure with the boron atom. The effect of this chelate improves the heat resistance, the chemical stability, and the hydrolysis resistance of this compound. The constant q of the ligand is 0 or 1. In particular, q is preferably 0 because the chelate ring becomes a five-membered ring and the chelate effect is most strongly achieved, improving the stability.

$Y^{53}$ and $Y^{54}$ are each individually a hydrogen atom, a C1-C10 alkyl group, a C1-C10 halogenated alkyl group, a C6-C20 aryl group, or a C6-C20 halogenated aryl group. These alkyl groups and aryl groups each may have a substituent or a hetero atom in the structure. When there are multiple $Y^{53}$'s or $Y^{54}$'s, they may be bonded to each other to form a ring.

The constant $m^{51}$ relating to the number of the aforementioned ligands is an integer of 1 or 2, preferably 2. The constant $n^{51}$ relating to the number of the aforementioned ligands is an integer of 0 to 8, preferably an integer of 0 to 4, more preferably 0 or 2. In addition, in formula (5), $n^{51}$ is preferably 2 when $m^{51}$ is 1, and $n^{51}$ is preferably 0 when $m^{51}$ is 2.

In formula (5), the alkyl group, the halogenated alkyl group, the aryl group, and the halogenated aryl group include those having other functional groups such as branches, hydroxy groups, and ether bonds.

Specific examples of the compound represented by formula (5) include lithium bis(oxalato)borate (LiBOB) represented by the following formula:

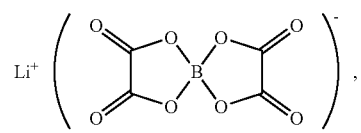

and lithium difluoro(oxalato)borate (LiDFOB) represented by the following formula:

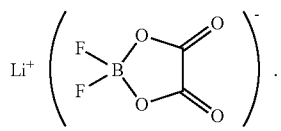

The electrolyte solution preferably contains the borate in an amount of 0.001 to 10% by mass relative to the electrolyte solution in order to further suppress a decrease in capacity retention and an increase in gas production even when stored at high temperatures. The lower limit of the amount of the borate is more preferably 0.1% by mass, still more preferably 0.3% by mass. The upper limit thereof is more preferably 3% by mass, still more preferably 2% by mass, particularly preferably 1% by mass.

The electrolyte solution of the present invention is preferably a non-aqueous electrolyte solution.

The electrolyte solution of the present invention preferably contains an electrolyte salt (excluding the borates described above).

The electrolyte salt may be any salt which can be used for electrolyte solutions, such as lithium salts, ammonium salts, and metal salts, as well as liquid salts (ionic liquid), inorganic polymeric salts, and organic polymeric salts.

The electrolyte salt of the electrolyte solution for lithium ion secondary batteries is preferably a lithium salt.

The lithium salt may be any lithium salt, and specific examples thereof include the following:

inorganic lithium salts such as $LiPF_6$, $LiBF_4$, $LiClO_4$, $LiAlF_4$, $LiSbF_6$, $LiTaF_6$, and $LiWF_7$;

lithium tungstates such as $LiWOF_5$;

lithium carboxylates such as $HCO_2Li$, $CH_3CO_2Li$, $CH_2FCO_2Li$, $CHF_2CO_2Li$, $CF_3CO_2Li$, $CF_3CH_2CO_2Li$, $CF_3CF_2CO_2Li$, $CF_3CF_2CF_2CO_2Li$, and $CF_3CF_2CF_2CF_2CO_2Li$;

lithium sulfonates such as $FSO_3Li$, $CH_3SO_3Li$, $CH_2FSO_3Li$, $CHF_2SO_3Li$, $CF_3SO_3Li$, $CF_3CF_2SO_3Li$, $CF_3CF_2CF_2SO_3Li$, and $CF_3CF_2CF_2CF_2SO_3Li$;

lithium imide salts such as $LiN(FCO)_2$, $LiN(FCO)(FSO_2)$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethanedisulfonylimide, lithium cyclic 1,3-perfluoropropanedisulfonylimide, and $LiN(CF_3SO_2)(C_4F_9SO_2)$;

lithium methide salts such as $LiC(FSO_2)_3$, $LiC(CF_3SO_2)_3$, and $LiC(C_2F_5SO_2)_3$;

lithium oxalatophosphate salts such as lithium tetrafluorooxalatophosphate, lithium difluorobis(oxalato)phosphate, and lithium tris(oxalato)phosphate; and fluoroorganic lithium salts such as salts represented by the formula: $LiPF_a(C_nF_{2n+1})_{6-a}$ wherein a is an integer of 0 to 5; n is an integer of 1 to 6) (e.g., $LiPF_4(CF_3)_2$, $LiPF_4(C_2F_5)_2$), $LiPF_4(CF_3SO_2)_2$, $LiPF_4(C_2F_5SO_2)_2$, $LiBF_3CF_3$, $LiBF_3C_2F_5$, $LiBF_3C_3F_7$, $LiBF_2(CF_3)_2$, $LiBF_2(C_2F)_2$, $LiBF_2(CF_3SO_2)_2$, and $LiBF_2(C_2F_5SO_2)_2$.

Particularly preferred are those such as $LiPF_6$, $LiBF_4$, $LiSbF_6$, $LiTaF_6$, $FSO_3Li$, $CF_3SO_3Li$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethanedisulfonylimide, lithium cyclic 1,3-perfluoropropanedisulfonylimide, $LiC(FSO_2)_3$, $LiC(CF_3SO_2)_3$, $LiC(C_2F_5SO_2)_3$, lithium tetrafluorooxalatophosphate, lithium difluorobis(oxalato)phosphate, $LiBF_3CF_3$, $LiBF_3C2F_5$, $LiPF_3(CF_3)_3$, and $LiPF_3(C_2F_5)_3$, for achieving effects of improving the characteristics such as output characteristics, high-rate charge and discharge characteristics, high-temperature storage characteristics, and cycle characteristics.

These lithium salts may be used alone or in combination of two or more. In the case of combination use of two or more lithium salts, examples of preferred combinations include a combination of $LiPF_6$ and $LiBF_4$ and a combination of $LiPF_6$ and $FSO_3Li$, which have effects of improving the load characteristics and the cycle characteristics.

The concentration of the electrolyte salt in the electrolyte solution is preferably 0.5 to 3 mol/L. If the concentration thereof is outside this range, the electric conductivity of the electrolyte solution tends to be low and the battery performance tends to be poor.

The concentration of the electrolyte salt is more preferably 0.9 mol/L or higher and 1.5 mol/L or lower.

The electrolyte salt of the electrolyte solution for electric double-layer capacitors is preferably an ammonium salt.

Examples of the ammonium salt include the following salts (IIa) to (IIe).

(IIa) Tetraalkyl Quaternary Ammonium Salts

Preferred examples thereof include tetraalkyl quaternary ammonium salts represented by formula (IIa) below:

wherein $R^{1a}$, $R^{2a}$, $R^{3a}$, and $R^{4a}$ are the same as or different from each other and are each a C1-C6 alkyl group optionally having an ether bond; and $X^-$ is an anion. The ammonium salts in which hydrogen atoms are partially or entirely replaced by fluorine atoms and/or C1-C4 fluoroalkyl groups are also preferred in order to improve the oxidation resistance.

Specific examples thereof include tetraalkyl quaternary ammonium salts represented by formula (IIa-1) below:

wherein $R^{1a}$, $R^{2a}$, and $X^-$ are as defined above; x and y are the same as or different from each other and are each an integer of 0 to 4, where x+y=4, and alkyl ether group-containing trialkyl ammonium salts represented by formula (IIa-2) below:

wherein $R^{5a}$ is a C1-C6 alkyl group; $R^{6a}$ is a C1-C6 divalent hydrocarbon group; $R^{7a}$ is a C1-C4 alkyl group; z is 1 or 2; and $X^-$ is an anion. Introduction of an alkyl ether group can reduce the viscosity.

The anion $X^-$ may be either an inorganic anion or an organic anion. Examples of the inorganic anion include $AlCl_4^-$, $BF_4^-$, $PF_6^-$, $AsF_6^-$, $TaF_6^-$, $I^-$, and $SbF_6^-$. Examples of the organic anion include $CF_3COO^-$, $CF_3SO_3^-$, $(CF_3SO_2)_2N^-$, and $(C_2F_5SO_2)_2N^-$.

Preferred among these are $BF_4^-$, $PF_6^-$, $AsF_6^-$, and $SbF_6^-$, in terms of good oxidation resistance and good ionic dissociation.

Preferred specific examples of the tetraalkyl quaternary ammonium salt include $Et_4NBF_4$, $Et_4NClO_4$, $Et_4NPF_6$, $Et_4NAsF_6$, $Et_4NSbF_6$, $Et_4NCF_3SO_3$, $Et_4N(CF_3SO_2)_2N$, $Et_4NC_4F_9SO_3$, $Et_3MeNBF_4$, $Et_3MeNClO_4$, $Et_3MeNPF_6$, $Et_3MeNAsF_6$, $Et_3MeNSbF_6$, $Et_3MeNCF_3SO_3$, $Et_3MeN(CF_3SO_2)_2N$, and $Et_3MeNC_4F_9SO_3$. Particularly preferred examples thereof include $Et_4NBF_4$, $Et_4NPF_6$, $Et_4NSbF_6$, $Et_4NAsF_6$, $Et_3MeNBF_4$, and N,N-diethyl-N-methyl-N-(2-methoxyethyl)ammonium salts.

(IIb) Spirocyclic Bipyrrolidinium Salts

Preferred examples thereof include spirocyclic bipyrrolidinium salts represented by formula (IIb-1) below:

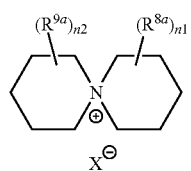

(IIb-1)

wherein $R^{8a}$ and $R^{9a}$ are the same as or different from each other and are each a C1-C4 alkyl group; $X^-$ is an anion; n1 is an integer of 0 to 5; and n2 is an integer of 0 to 5); spirocyclic bipyrrolidinium salts represented by (IIb-2) below:

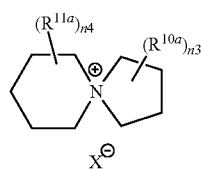

(IIb-2)

wherein $R^{10a}$ and $R^{11a}$ are the same as or different from each other and are each a C1-C4 alkyl group; $X^-$ is an anion; n3 is an integer of 0 to 5; and n4 is an integer of 0 to 5); and spirocyclic bipyrrolidinium salts represented by formula (IIb-3) below:

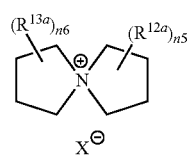

(IIb-3)

wherein $R^{12a}$ and $R^{13a}$ are the same as or different from each other and are each a C1-C4 alkyl group; $X^-$ is an anion; n5 is an integer of 0 to 5; and n6 is an integer of 0 to 5). The spirocyclic bipyrrolidinium salts in which hydrogen atoms are partially or entirely replaced by fluorine atoms and/or C1-C4 fluoroalkyl groups are also preferred for improving the oxidation resistance.

Preferred specific examples of the anion $X^-$ are the same as those mentioned for the salts (IIa). In particular, $BF_4^-$, $PF_6^-$, $(CF_3SO_2)_2N^-$, and $(C_2F_5SO_2)_2N^-$ are preferred in terms of high dissociation and a low internal resistance under high voltage.

Preferred specific examples of the spirocyclic bipyrrolidinium salt include those represented by the following formulas:

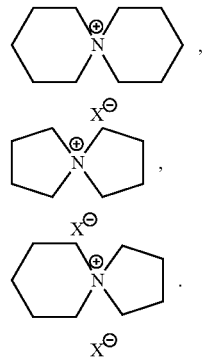

These spirocyclic bipyrrolidinium salts are excellent in terms of solubility in a solvent, oxidation resistance, and ion conductivity.

(IIc) Imidazolium Salts

Preferred examples thereof include imidazolium salts represented by formula (IIc) below:

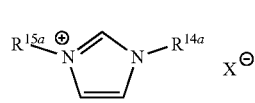

(IIc)

wherein $R^{14a}$ and $R^{15a}$ are the same as or different from each other and are each a C1-C6 alkyl group; and $X^-$ is an anion. The imidazolium salts in which hydrogen atoms are partially or entirely replaced by fluorine atoms and/or C1-C4 fluoroalkyl groups are also preferred in order to improve the oxidation resistance.

Preferred specific examples of the anion $X^-$ are the same as those mentioned for the salts (IIa).

Preferred specific examples include one represented by the following formula:

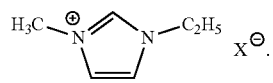

This imidazolium salt is excellent in terms of low viscosity and good solubility.

(IId): N-Alkylpyridinium Salts

Preferred examples thereof include N-alkylpyridinium salts represented by formula (IId) below:

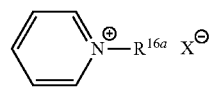

(IId)

wherein $R^{16a}$ is a C1-C6 alkyl group; and $X^-$ is an anion) The N-alkylpyridinium salts in which hydrogen atoms are partially or entirely replaced by fluorine atoms and/or C1-C4 fluoroalkyl groups are also preferred in order to improve the oxidation resistance.

Preferred specific examples of the anion $X^-$ are the same as those mentioned for the salts (IIa).

Preferred specific examples include those represented by the following formulas:

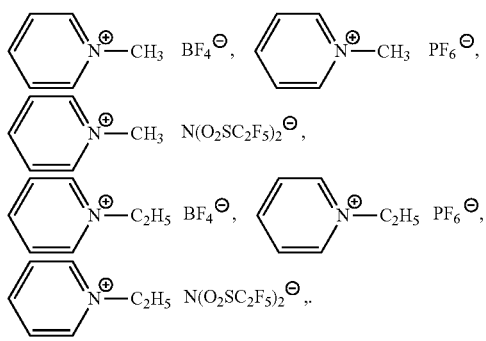

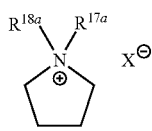

These N-alkylpyridinium salts are excellent in terms of low viscosity and good solubility.

(IIe) N,N-Dialkylpyrrolidinium Salts

Preferred examples thereof include N,N-dialkylpyrrolidinium salts represented by formula (IIe) below:

$$R^{18a} \quad R^{17a}$$
(IIe)

wherein $R^{17a}$ and $R1^{sa}$ are the same as or different from each other and are each a C1-C6 alkyl group; and $X^-$ is an anion. The N,N-dialkylpyrrolidinium salts in which the hydrogen atoms are partially or entirely replaced by fluorine atoms and/or C1-C4 fluoroalkyl groups are also preferred in order to improve the oxidation resistance.

Preferred specific examples of the anion $X^-$ are the same as those mentioned for the salts (IIa).

Preferred specific examples include those represented by the following formulas:

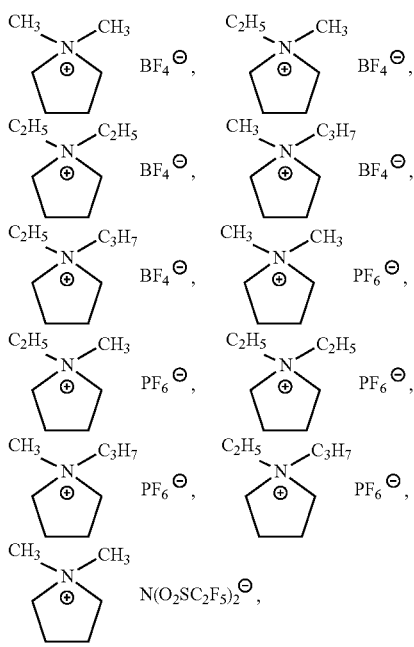

These N,N-dialkylpyrrolidinium salts are excellent in terms of low viscosity and good solubility.

Preferred among these ammonium salts are those represented by formula (IIa), (IIb), or (IIc) because they have good solubility, oxidation resistance, and ion conductivity. More preferred are those represented by any of the following formulas:

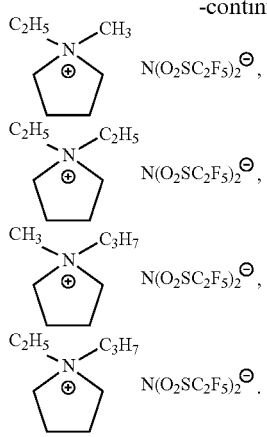

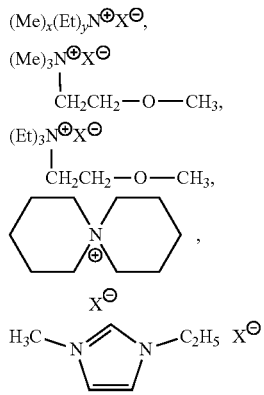

wherein Me is a methyl group; Et is an ethyl group; X, x, and y are as defined above for formula (IIa-1).

The electrolyte salt for electric double-layer capacitors may be a lithium salt. Preferred examples of the lithium salt include $LiPF_6$, $LiBF_4$, $LiAsF_6$, $LiSbF_6$, and $LiN(SO_2C_2H_5)_2$.

In order to further increase the capacity, a magnesium salt may be used. Preferred examples of the magnesium salt include $Mg(ClO_4)_2$ and $Mg(OOC_2H_5)_2$.

If the electrolyte salt is any of the above ammonium salts, the concentration thereof is preferably 0.6 mol/L or higher. If the concentration thereof is lower than 0.6 mol/L, the low-temperature characteristics may be poor, and the initial internal resistance may be high. The concentration of the electrolyte salt is more preferably 0.9 mol/L or higher.

In terms of low-temperature characteristics, the concentration is preferably 3.0 mol/L or lower, more preferably 2 mol/L or lower.

If the ammonium salt is triethyl methyl ammonium tetrafluoroborate ($TEMABF_4$), the concentration thereof is preferably 0.8 to 1.9 mol/L in terms of excellent low-temperature characteristics.

If the ammonium salt is spirobipyrrolidinium tetrafluoroborate (SBPBF$_4$), the concentration thereof is preferably 0.7 to 2.0 mol/L.

The electrolyte solution of the present invention preferably further includes polyethylene oxide having a weight average molecular weight of 2000 to 4000 and containing —OH, —OCOOH, or —COOH at an end.

The presence of such a compound can improve the stability at the electrode interface and thus can improve characteristics of electrochemical devices.

Examples of the polyethylene oxide include polyethylene oxide monool, polyethylene oxide carboxylate, polyethylene oxide diol, polyethylene oxide dicarboxylate, polyethylene oxide triol, and polyethylene oxide tricarboxylate. These may be used alone or in combination of two or more.

In particular, a mixture of polyethylene oxide monool and polyethylene oxide diol and a mixture of polyethylene oxide carboxylate and polyethylene oxide dicarboxylate are preferred in order to further improve the characteristics of electrochemical devices.

The polyethylene oxide having too small a weight average molecular weight may be easily oxidatively decomposed. The weight average molecular weight is more preferably 3000 to 4000.

The weight average molecular weight can be determined in terms of polystyrene equivalent by gel permeation chromatography (GPC).

The amount of the polyethylene oxide is preferably $1 \times 10^{-6}$ to $1 \times 10^{-2}$ mol/kg in the electrolyte solution. If the amount of the polyethylene oxide is too large, characteristics of electrochemical devices may be impaired.

The amount of the polyethylene oxide is more preferably $5 \times 10^{-6}$ mol/kg or more.

The electrolyte solution of the present invention may further contain other additives such as unsaturated cyclic carbonate, overcharge inhibitors, and other known auxiliary agents. This enables suppression of a decrease in characteristics of electrochemical devices.

Examples of the unsaturated cyclic carbonate include vinylene carbonates, ethylene carbonates substituted with a substituent having an aromatic ring, a carbon-carbon double bond, or a carbon-carbon triple bond, phenyl carbonates, vinyl carbonates, allyl carbonates, and catechol carbonates.

Examples of the vinylene carbonates include vinylene carbonate, methyl vinylene carbonate, 4,5-dimethyl vinylene carbonate, phenyl vinylene carbonate, 4,5-diphenyl vinylene carbonate, vinyl vinylene carbonate, 4,5-divinyl vinylene carbonate, allyl vinylene carbonate, 4,5-diallyl vinylene carbonate, 4-fluorovinylene carbonate, 4-fluoro-5-methyl vinylene carbonate, 4-fluoro-5-phenyl vinylene carbonate, 4-fluoro-5-vinyl vinylene carbonate, and 4-allyl-5-fluorovinylene carbonate.

Specific examples of the ethylene carbonates substituted with a substituent having an aromatic ring, a carbon-carbon double bond, or a carbon-carbon triple bond include vinyl ethylene carbonate, 4,5-divinyl ethylene carbonate, 4-methyl-5-vinyl ethylene carbonate, 4-allyl-5-vinyl ethylene carbonate, ethynyl ethylene carbonate, 4,5-diethynyl ethylene carbonate, 4-methyl-5-ethynyl ethylene carbonate, 4-vinyl-5-ethynyl ethylene carbonate, 4-allyl-5-ethynyl ethylene carbonate, phenyl ethylene carbonate, 4,5-diphenyl ethylene carbonate, 4-phenyl-5-vinyl ethylene carbonate, 4-allyl-5-phenyl ethylene carbonate, allyl ethylene carbonate, 4,5-diallyl ethylene carbonate, and 4-methyl-5-allyl ethylene carbonate.

The unsaturated cyclic carbonates are particularly preferably vinylene carbonate, methyl vinylene carbonate, 4,5-dimethyl vinylene carbonate, vinyl vinylene carbonate, 4,5-vinyl vinylene carbonate, allyl vinylene carbonate, 4,5-diallyl vinylene carbonate, vinyl ethylene carbonate, 4,5-divinyl ethylene carbonate, 4-methyl-5-vinyl ethylene carbonate, allyl ethylene carbonate, 4,5-diallyl ethylene carbonate, 4-methyl-5-allyl ethylene carbonate, 4-allyl-5-vinyl ethylene carbonate, ethynyl ethylene carbonate, 4,5-diethynyl ethylene carbonate, 4-methyl-5-ethynyl ethylene carbonate, and 4-vinyl-5-ethynyl ethylene carbonate. Vinylene carbonate, vinyl ethylene carbonate, and ethynyl ethylene carbonate are also particularly preferred because they form a more stable interface protective coating film.

The unsaturated cyclic carbonate may have any molecular weight that does not significantly impair the effects of the present invention. The molecular weight is preferably 80 or higher and 250 or lower. The unsaturated cyclic carbonate having a molecular weight within this range is likely to ensure the solubility of the fluorinated unsaturated cyclic carbonate in the non-aqueous electrolyte solution and enable sufficient achievement of the effects of the present invention. The molecular weight of the unsaturated cyclic carbonate is more preferably 85 or higher and 150 or lower.

The unsaturated cyclic carbonate may be produced by any method, and can be produced by any known appropriately selected method.

These unsaturated cyclic carbonates may be used alone or in any combination of two or more at any ratio.

The unsaturated cyclic carbonate may be in any amount that does not significantly impair the effects of the present invention. The amount of the unsaturated cyclic carbonate is preferably 0.001% by mass or more, more preferably 0.1% by mass or more, still more preferably 0.5% by mass or more, in 100% by mass of the solvent in the present invention. The amount thereof is also preferably 5% by mass or less, more preferably 3% by mass or less, still more preferably 2% by mass or less. An amount within the above range allows an electrochemical device containing the electrolyte solution to easily exert a sufficient effect of improving the cycle characteristics, and makes it easy to avoid a decrease in high-temperature storage characteristics, an increase in gas production, and a decrease in discharge capacity retention.

A fluorinated unsaturated cyclic carbonate can also be suitably used as the unsaturated cyclic carbonate, in addition to the non-fluorinated unsaturated cyclic carbonates described above.

The fluorinated unsaturated cyclic carbonate is a cyclic carbonate having an unsaturated bond and a fluorine atom. The number of fluorine atoms in the fluorinated unsaturated cyclic carbonate may be any number that is 1 or greater. The number of fluorine atoms is usually 6 or smaller, preferably 4 or smaller, most preferably 1 or 2.

Examples of the fluorinated unsaturated cyclic carbonate include fluorinated vinylene carbonate derivatives and fluorinated ethylene carbonate derivatives substituted with a substituent having an aromatic ring or a carbon-carbon double bond.

Examples of the fluorinated vinylene carbonate derivatives include 4-fluorovinylene carbonate, 4-fluoro-5-methyl vinylene carbonate, 4-fluoro-5-phenyl vinylene carbonate, 4-allyl-5-fluorovinylene carbonate, and 4-fluoro-5-vinyl vinylene carbonate.

Examples of the fluorinated ethylene carbonate derivatives substituted with a substituent having an aromatic ring or a carbon-carbon double bond include 4-fluoro-4-vinyl ethylene carbonate, 4-fluoro-4-allyl ethylene carbonate, 4-fluoro-5-vinyl ethylene carbonate, 4-fluoro-5-allyl ethylene carbonate, 4,4-difluoro-4-vinyl ethylene carbonate, 4,4-difluoro-4-allyl ethylene carbonate, 4,5-difluoro-4-vinyl ethylene carbonate, 4,5-difluoro-4-allyl ethylene carbonate, 4-fluoro-4,5-divinyl ethylene carbonate, 4-fluoro-4,5-diallyl ethylene carbonate, 4,5-difluoro-4,5-divinyl ethylene carbonate, 4,5-difluoro-4,5-diallyl ethylene carbonate, 4-fluoro-4-phenyl ethylene carbonate, 4-fluoro-5-phenyl ethylene carbonate, 4,4-difluoro-5-phenyl ethylene carbonate, and 4,5-difluoro-4-phenyl ethylene carbonate.

More preferred fluorinated unsaturated cyclic carbonates to be used are 4-fluorovinylene carbonate, 4-fluoro-5-methyl vinylene carbonate, 4-fluoro-5-vinyl vinylene carbonate, 4-allyl-5-fluorovinylene carbonate, 4-fluoro-4-vinyl ethylene carbonate, 4-fluoro-4-allyl ethylene carbonate, 4-fluoro-5-vinyl ethylene carbonate, 4-fluoro-5-allyl ethylene carbonate, 4,4-difluoro-4-vinyl ethylene carbonate, 4,4-difluoro-4-allyl ethylene carbonate, 4,5-difluoro-4-vinyl ethylene carbonate, 4,5-difluoro-4-allyl ethylene carbonate, 4-fluoro-4,5-divinyl ethylene carbonate, 4-fluoro-4,5-diallyl ethylene carbonate, 4,5-difluoro-4,5-divinyl ethylene carbonate, and 4,5-difluoro-4,5-diallyl ethylene carbonate, because they form a stable interface protective coating film.

The fluorinated unsaturated cyclic carbonate may have any molecular weight that does not significantly impair the effects of the present invention. The molecular weight is preferably 50 or higher and 250 or lower. The fluorinated unsaturated cyclic carbonate having a molecular weight within this range is likely to ensure the solubility of the fluorinated unsaturated cyclic carbonate in the electrolyte solution and enable achievement of the effects of the present invention.

The fluorinated unsaturated cyclic carbonate may be produced by any method, and can be produced by any known appropriately selected method. The molecular weight thereof is more preferably 100 or more and 200 or less.

The above fluorinated unsaturated cyclic carbonates may be used alone or in any combination of two or more at any ratio. The fluorinated unsaturated cyclic carbonate may be in any amount that does not significantly impair the effects of the present invention. The amount of the fluorinated unsaturated cyclic carbonate is usually preferably 0.01% by mass or more, more preferably 0.1% by mass or more, still more preferably 0.5% by mass or more, while it is preferably 5% by mass or less, more preferably 3% by mass or less, still more preferably 2% by mass or less, in 100% by mass of the electrolyte solution. An amount within the above range allows an electrochemical device containing the electrolyte solution to easily exert a sufficient effect of improving the cycle characteristics, and makes it easy to avoid a decrease in high-temperature storage characteristics, an increase in gas production, and a decrease in discharge capacity retention.

The electrolyte solution of the present invention may contain an overcharge inhibitor in order to effectively suppress burst or combustion of batteries in case of, for example, overcharge of electrochemical devices containing the electrolyte solution.

Examples of the overcharge inhibitor include aromatic compounds such as biphenyl, alkyl biphenyl, terphenyl, partially hydrogenated terphenyl, cyclohexyl benzene, t-butyl benzene, t-amyl benzene, diphenyl ether, and dibenzofuran; partially fluorinated products of the above aromatic compounds such as 2-fluorobiphenyl, o-cyclohexyl fluorobenzene, and p-cyclohexyl fluorobenzene; and fluoroanisole compounds such as 2,4-difluoroanisole, 2,5-difluoroanisole, 2,6-difluoroanisole, and 3,5-difluoroanisole. Preferred are aromatic compounds such as biphenyl, alkyl biphenyl, terphenyl, partially hydrogenated terphenyl, cyclohexyl benzene, t-butyl benzene, t-amyl benzene, diphenyl ether, and dibenzofuran. These compounds may be used alone or in combination of two or more. In the case of combination use of two or more compounds, preferred is a combination of cyclohexyl benzene and t-butyl benzene or t-amyl benzene, or a combination of at least one oxygen-free aromatic compound selected from biphenyl, alkyl biphenyl, terphenyl, partially hydrogenated terphenyl, cyclohexyl benzene, t-butyl benzene, t-amyl benzene, and the like, and at least one oxygen-containing aromatic compound selected from diphenyl ether, dibenzofuran, and the like. Such combinations are preferred because they lead to good balance between the overcharge inhibiting characteristics and the high-temperature storage characteristics.

The electrolyte solution of the present invention may further contain any other known auxiliary agent. Examples of the auxiliary agent include carbonate compounds such as erythritan carbonate, spiro-bis-dimethylene carbonate, and methoxy ethyl-methyl carbonate; spiro compounds such as 2,4,8,10-tetraoxaspiro[5.5]undecane and 3,9-divinyl-2,4,8,10-tetraoxaspiro[5.5]undecane; sulfur-containing compounds such as ethylene sulfite, 1,3-propanesultone, 1-fluoro-1,3-propanesultone, 2-fluoro-1,3-propanesultone, 3-fluoro-1,3-propanesultone, 1-propene-1,3-sultone, 1-fluoro-1-propene-1,3-sultone, 2-fluoro-1-propene-1,3-sultone, 3-fluoro-1-propene-1,3-sultone, 1,4-butanesultone, 1-butene-1,4-sultone, 3-butene-1,4-sultone, methyl fluorosulfonate, ethyl fluorosulfonate, methyl methanesulfonate, ethyl methanesulfonate, busulfan, sulfolene, diphenyl sulfone, N,N-dimethyl methanesulfonamide, N,N-diethyl methanesulfonamide, methyl vinylsulfonate, ethyl vinylsulfonate, allyl vinylsulfonate, propargyl vinylsulfonate, methyl allylsulfonate, ethyl allylsulfonate, allyl allylsulfonate, propargyl allylsulfonate, and 1,2-bis(vinylsulfonyloxy)ethane; nitrogen-containing compounds such as 1-methyl-2-pyrrolidinone, 1-methyl-2-piperidone, 3-methyl-2-oxazolidinone, 1,3-dimethyl-2-imidazolidinone, and N-methylsuccinimide; phosphorous-containing compounds such as trimethyl phosphite, triethyl phosphite, triphenyl phosphite, trimethyl phosphate, triethyl phosphate, triphenyl phosphate, dimethyl methylphosphonate, diethyl ethylphosphonate, dimethyl vinylphosphonate, diethyl vinylphosphonate, ethyl diethylphosphonoacetate, methyl dimethylphosphinate, ethyl diethylphosphinate, trimethylphosphine oxide, and triethylphosphine oxide; hydrocarbon compounds such as heptane, octane, nonane, decane, and cycloheptane; and fluoroaromatic compounds such as fluorobenzene, difluorobenzene, hexafluorobenzene, and benzotrifluoride. These auxiliary agents may be used alone or in combination of two or more. Adding any of these auxiliary agents can improve the capacity retention characteristics and cycle characteristics after high-temperature storage.

The auxiliary agent may be used in any amount that does not significantly impair the effects of the present invention. The amount of the auxiliary agent is preferably 0.01% by mass or more and 5% by mass or less in 100% by mass of the electrolyte solution. The auxiliary agent in an amount within this range is likely to sufficiently exert its effects and may make it easy to avoid a decrease in battery characteristics such as high-load discharge characteristics. The amount of the auxiliary agent is more preferably 0.1% by mass or more, still more preferably 0.2% by mass or more, while it is more preferably 3% by mass or less, still more preferably 1% by mass or less.

The electrolyte solution of the present invention may further contain any of cyclic or acyclic carboxylic acid esters, ether compounds, nitrogen-containing compounds, boron-containing compounds, organic silicon-containing compounds, fireproof agents (flame retardants), surfactants, permittivity-improving additives, and improvers for cycle characteristics and rate characteristics, to the extent that does not impair the effects of the present invention.

Examples of the cyclic carboxylic acid esters include those having a total of 3 to 12 carbon atoms in the structural formula. Specific examples thereof include gamma-butyrolactone, gamma-valerolactone, gamma-caprolactone, and epsilon-caprolactone. Particularly preferred is gamma-butyrolactone because it can improve the characteristics of electrochemical devices owing to improvement in the degree of dissociation of lithium ions.

In general, the amount of the cyclic carboxylic acid ester is preferably 0.1% by mass or more, more preferably 1% by mass or more, in 100% by mass of the solvent. The cyclic carboxylic acid ester in an amount within this range is likely to improve the electric conductivity of the electrolyte solution, and thus to improve the large-current discharge characteristics of electrochemical devices. The amount of the cyclic carboxylic acid ester is also preferably 10% by mass or less, more preferably 5% by mass or less. Such an upper limit may allow the electrolyte solution to have a viscosity within an appropriate range, may make it possible to avoid a decrease in electric conductivity, may suppress an increase in resistance of a negative electrode, and may allow an electrochemical device to have large-current discharge characteristics within a favorable range.

The cyclic carboxylic acid ester to be suitably used may be a fluorinated cyclic carboxylic acid ester (fluorolactone). Examples of the fluorolactone include fluorolactones represented by formula (C) below:

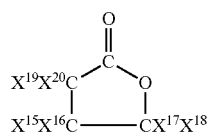

(C)

wherein $X^{15}$ to $X^{20}$ are the same as or different from each other and are each —H, —F, —Cl, —CH$_3$, or a fluorinated alkyl group, with at least one of $X^{15}$ to $X^{20}$ being a fluorinated alkyl group.

Examples of the fluorinated alkyl group for $X^{15}$ to $X^{20}$ include —CFH$_2$, —CF$_2$H, —CF$_3$, —CH$_2$CF$_3$, —CF$_2$CF$_3$, —CH$_2$CF$_2$CF$_3$, and —CF(CF$_3$)$_2$. Preferred are —CH$_2$CF$_3$ and —CH$_2$CF$_2$CF$_3$ in terms of high oxidation resistance and an effect of improving the safety.

As long as at least one of $X^{15}$ to $X^{20}$ is a fluorinated alkyl group, —H, —F, —Cl, —CH$_3$ or a fluorinated alkyl group may substitute for one of $X^{15}$ to $X^{20}$ or a plurality thereof. In terms of good solubility of the electrolyte salt, they preferably substitute for 1 to 3 sites, more preferably 1 or 2 site(s).

The substitution site of the fluorinated alkyl group may be at any of the above sites. In terms of good synthesizing yield, the substitution site is preferably $X^{17}$ and/or $X^{18}$. In particular, $X^{17}$ or $X^{18}$ is preferably a fluorinated alkyl group, especially, —CH$_2$CF$_3$ or —CH$_2$CF$_2$CF$_3$. The substituent for $X^{15}$ to $X^{20}$ other than the fluorinated alkyl group is —H, —F, —Cl, or CH$_3$. In particularly, —H is preferred in terms of good solubility of the electrolyte salt.

In addition to those represented by the above formula, examples of the fluorolactone may also include fluorolactones represented by formula (D) below:

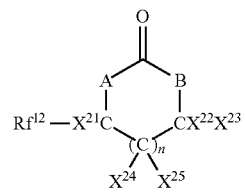

(D)

wherein one of A and B is $CX^{26}X^{27}$ (where $X^{26}$ and $X^{27}$ are the same as or different from each other and are each —H, —F, —Cl, —CF$_3$, —CH$_3$, or an alkylene group in which one or more hydrogen atoms are optionally replaced by halogen atoms and which optionally has a hetero atom in the chain) and the other is an oxygen atom; $Rf^{12}$ is a fluorinated alkyl group or fluorinated alkoxy group optionally having an ether bond; $X^{21}$ and $X^{22}$ are the same as or different from each other and are each —H, —F, —Cl, —CF$_3$, or CH$_3$; $X^{23}$ to $X^{25}$ are the same as or different from each other and are each —H, —F, —Cl, or an alkyl group in which one or more hydrogen atoms are optionally replaced by halogen atoms and which optionally has a hetero atom in the chain; and n=0 or 1.

Preferred examples of the fluorolactone represented by formula (D) include 5-membered ring structures represented by formula (E) below:

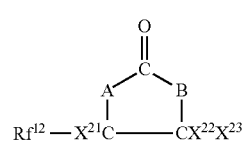

(E)

wherein A, B, $Rf^2$, $X^{21}$, $X^{22}$, and $X^{23}$ are as defined above for formula (D). This compound is preferred because it is easily synthesized and has good chemical stability. Further, in relation to the combination of A and B, fluorolactones represented by formula (F) below:

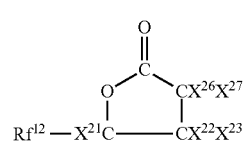

(F)

wherein $Rf^{12}$, $X^{21}$, $X^{22}$, $X^{23}$, $X^{26}$, and $X^{27}$ are as defined above for formula (D); and fluorolactones represented by formula (G) below:

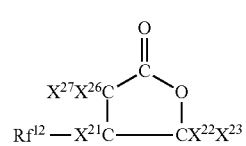

(G)

wherein $Rf^{12}$, $X^{21}$, $X^{22}$, $X^{23}$, $X^{26}$, and $X^{27}$ are as defined above for formula (D)

In particular, in order to achieve excellent characteristics such as a high permittivity and a high withstand voltage and to improve the characteristics of the electrolyte solution of the present invention in terms of good solubility of the electrolyte salt and low internal resistance, those represented by the following formulas may be mentioned:

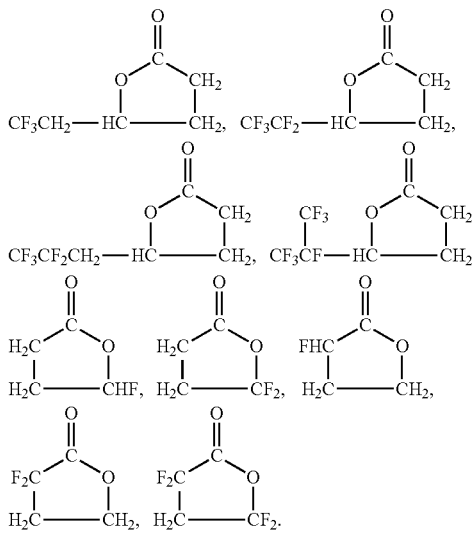

The presence of a fluorinated cyclic carboxylic acid ester leads to effects of, for example, improving the ion conductivity, improving the safety, and improving the stability at high temperatures.

Examples of the acyclic carboxylic acid ester include those having a total of 3 to 7 carbon atoms in the structural formula. Specific examples thereof include methyl acetate, ethyl acetate, n-propyl acetate, isopropyl acetate, n-butyl acetate, isobutyl acetate, t-butyl acetate, methyl propionate, ethyl propionate, n-propyl propionate, isopropyl propionate, n-butyl propionate, isobutyl propionate, t-butyl propionate, methyl butyrate, ethyl butyrate, n-propyl butyrate, isopropyl butyrate, methyl isobutyrate, ethyl isobutyrate, n-propyl isobutyrate, and isopropyl isobutyrate.

In particular, those such as methyl acetate, ethyl acetate, n-propyl acetate, n-butyl acetate, methyl propionate, ethyl propionate, n-propyl propionate, isopropyl propionate, methyl butyrate, and ethyl butyrate are preferred in order to improve the ion conductivity owing to a decrease in viscosity.

The ether compound is preferably a C3-C10 acyclic ether or a C3-C6 cyclic ether.

Examples of the C3-C10 acyclic ether include diethyl ether, di-n-butyl ether, dimethoxy methane, methoxy ethoxy methane, diethoxy methane, dimethoxy ethane, methoxy ethoxy ethane, diethoxy ethane, ethylene glycol di-n-propyl ether, ethylene glycol di-n-butyl ether, and diethylene glycol dimethyl ether.

The ether compound may suitably be a fluorinated ether.

One example of the fluorinated ether is a fluorinated ether (I) represented by formula (I) below:

wherein $Rf^3$ and $Rf^4$ are the same as or different from each other and are each a C1-C10 alkyl group or a C1-C10 fluorinated alkyl group, with at least one of $Rf^3$ and $Rf^4$ being a fluorinated alkyl group. The presence of the fluorinated ether (I) can improve the incombustibility of the electrolyte solution, as well as the stability and safety at high temperatures and high voltages.

In formula (I), it suffices as long as at least one of $Rf^3$ and $Rf^4$ is a C1-C10 fluorinated alkyl group. In order to further improve the incombustibility and the stability and safety at high temperature and high voltage of the electrolyte solution, both $Rf^3$ and $Rf^4$ are preferably a C1-C10 fluorinated alkyl group. In this case, $Rf^3$ and $Rf^4$ may be the same as or different from each other.

In particular, more preferably, $Rf^3$ and $Rf^4$ are the same as or different from each other, and $Rf^3$ is a C3-C6 fluorinated alkyl group and $Rf^4$ is a C2-C6 fluorinated alkyl group.

If the sum of the carbon numbers of $Rf^3$ and $Rf^4$ is too small, the fluorinated ether may have too low a boiling point. If the carbon number of $Rf^3$ or $Rf^4$ is too large, the solubility of the electrolyte salt may be low, which may have an adverse influence on the compatibility with other solvents, and the viscosity may be high so that the rate characteristics may be poor. When the carbon number of $Rf^3$ is 3 or 4 and the carbon number of $Rf^4$ is 2 or 3, it is advantageous in terms of excellent boiling point and rate characteristics.

The fluorinated ether (I) preferably has a fluorine content of 40 to 75% by mass. The fluorinated ether (I) having a fluorine content within this range may lead to particularly excellent balance between the incombustibility and the compatibility. The above range is also preferred in terms of good oxidation resistance and safety.

The lower limit of the fluorine content is more preferably 45% by mass, still more preferably 50% by mass, particularly preferably 55% by mass. The upper limit thereof is more preferably 70% by mass, still more preferably 66% by mass.

The fluorine content of the fluorinated ether (I) is a value calculated based on the structural formula of the fluorinated ether (I) by the formula:

{(Number of fluorine atoms×19)/(Molecular weight of fluorinated ether (I))}×100(%).

Examples of $Rf^3$ include $CF_3CF_2CH_2$—, $CF_3CFHCF_2$—, $HCF_2CF_2CF_2$—, $HCF_2CF_2CH_2$—, $CF_3CF_2CH_2CH_2$—, $CF_3CFHCF_2CH_2$—, $HCF_2CF_2CF_2CF_2$—, $HCF_2CF_2CF_2CH_2$—, $HCF_2CF_2CH_2CH_2$—, and $HCF_2CF(CF_3)CH_2$—. Examples of $Rf^4$ include —$CH_2CF_2CF_3$, —$CF_2CFHCF_3$, —$CF_2CF_2CF_2H$, —$CH_2CF_2CF_2H$, —$CH_2CH_2CF_2CF_3$, —$CH_2CF_2CFHCF_3$, —$CF_2CF_2CF_2CF_2H$, —$CH_2CF_2CF_2CF_2H$, —$CH_2CH_2CF_2CF_2H$, —$CH_2CF(CF_3)CF_2H$, —$CF_2CF_2H$, —$CH_2CF_2H$, and —$CF_2CH_3$.

Specific examples of the fluorinated ether (I) include $HCF_2CF_2CH_2OCF_2CF_2H$, $CF_3CF_2CH_2OCF_2CF_2H$, $HCF_2CF_2CH_2OCF_2CFHCF_3$, $CF_3CF_2CH_2OCF_2CFHCF_3$, $C_6F_{13}OCH_3$, $C_6F_{13}OC_2H_5$, $C_8F_{17}OCH_3$, $C_8F_{17}OC_2H_5$, $CF_3CFHCF_2CH(CH_3)$ $OCF_2CFHCF_3$, $HCF_2CF_2OCH(C_2H_5)_2$, $HCF_2CF_2OC_4H_9$, $HCF_2CF_2OCH_2CH(C_2H_5)_2$, and $HCF_2CF_2OCH_2CH(CH_3)_2$.

In particular, with those having $HCF_2$— or $CF_3CFH$— at one end or both ends, the fluorinated ether (I) excellent in polarizability and having a high boiling point can be provided. The boiling point of the fluorinated ether (I) is preferably 67° C. to 120° C. It is more preferably 80° C. or higher, still more preferably 90° C. or higher.

Examples of the fluorinated ether (I) include one or two or more of $CF_3CH_2OCF_2CFHCF_3$, $CF_3CF_2CH_2OCF_2CFHCF_3$, $HCF_2CF_2CH_2OCF_2CFHCF_3$, $HCF_2CF_2CH_2OCH_2CF_2CF_2H$, $CF_3CFHCF_2CH_2OCF_2CFHCF_3$, $HCF_2CF_2CH_2OCF_2CF_2H$, and $CF_3CF_2CH_2OCF_2CF_2H$.

In particular, to provide advantages in terms of a high boiling point, good compatibility with other solvents, and a good solubility of the electrolyte salt, the fluorinated ether (I) is preferably at least one selected from the group consisting of $HCF_2CF_2CH_2OCF_2CFHCF_3$ (boiling point: 106° C.), $CF_3CF_2CH_2OCF_2CFHCF_3$ (boiling point: 82° C.), $HCF_2CF_2CH_2OCF_2CF_2H$ (boiling point: 92° C.), and $CF_3CF_2CH_2OCF_2CF_2H$ (boiling point: 68° C.), more preferably at least one selected from the group consisting of $HCF_2CF_2CH_2OCF_2CFHCF_3$ (boiling point: 106° C.) and $HCF_2CF_2CH_2OCF_2CF_2H$ (boiling point: 92° C.)

Examples of the C3-C6 cyclic ether include 1,3-dioxane, 2-methyl-1,3-dioxane, 4-methyl-1,3-dioxane, 1,4-dioxane, and fluorinated compounds thereof. Preferred are dimethoxy methane, diethoxy methane, ethoxy methoxy methane, ethylene glycol n-propyl ether, ethylene glycol di-n-butyl ether, and diethylene glycol dimethyl ether because they have a high ability to solvate lithium ions and improve the degree of ion dissociation. Particularly preferred are dimethoxy methane, diethoxy methane, and ethoxy methoxy methane because they have a low viscosity and give a high ion conductivity.

Examples of the nitrogen-containing compounds include nitrile, fluorine-containing nitrile, carboxylic acid amide, fluorine-containing carboxylic acid amide, sulfonic acid amide, and fluorine-containing sulfonic acid amide. In addition, 1-methyl-2-pyrrolidinone, 1-methyl-2-piperidone, 3-methyl-2-oxazilidinone, 1,3-dimethyl-2-imidazolidinone, and N-methylsuccinimide may also be used.

Examples of the boron-containing compounds include boric acid esters such as trimethyl borate and triethyl borate, boric acid ethers, and alkyl borates.

Examples of the organic silicon-containing compounds include $(CH_3)_4$—Si and $(CH_3)_3$—Si—Si$(CH_3)_3$.

Examples of the fireproof agents (flame retardants) include phosphoric acid esters and phosphazene-based compounds. Examples of the phosphoric acid esters include fluoroalkyl phosphates, non-fluoroalkyl phosphates, and aryl phosphates. Particularly preferred are fluoroalkyl phosphates because they can show an incombustible effect even with a small amount.

Specific examples of the fluoroalkyl phosphates include fluorodialkyl phosphates disclosed in JP H11-233141 A, cyclic alkyl phosphates disclosed in JP H11-283669 A, and fluorotrialkyl phosphates.

Preferred as the fireproof agents (flame retardants) are those such as $(CH_3O)_3P=O$, $(CF_3CH_2O)_3P=O$, $(HCF_2CH_2O)_3P=O$, $(CF_3CF_2CH_2)_3P=O$, and $(HCF_2CF_2CH_2)_3P=O$.

The surfactant may be any of cationic surfactants, anionic surfactants, nonionic surfactants, and amphoteric surfactants. In terms of good cycle characteristics and rate characteristics, the surfactant is preferably one containing a fluorine atom.

Preferred examples of such a surfactant containing a fluorine atom include fluorine-containing carboxylic acid salts represented by the following formula:

$Rf^5COO^-M^+$ wherein $Rf^5$ is a C3-C10 fluoroalkyl group optionally having an ether bond; and $M^+$ is $Li^+$, $Na^+$, $K^+$, or $NHR'_3{}^+$ (where R's are the same as or different from each other and are each H or a C1-C3 alkyl group); and fluorine-containing sulfonic acid salts represented by the following formula:

$Rf^6SO_3{}^-M^+$ wherein $Rf^6$ is a C3-C10 fluoroalkyl group optionally having an ether bond; and $M^+$ is $Li^+$, $Na^+$, $K^+$, or $NHR'_3{}^+$ (where R's are the same as or different from each other and are each H or a C1-C3 alkyl group).

The amount of the surfactant is preferably 0.01 to 2% by mass in the electrolyte solution in order to reduce the surface tension of the electrolyte solution without degrading the charge and discharge cycle characteristics.

Examples of the permittivity-improving additives include sulfolane, methyl sulfolane, γ-butyrolactone, γ-valerolactone, acetonitrile, and propionitrile.

Examples of the improvers for cycle characteristics and rate characteristics include methyl acetate, ethyl acetate, tetrahydrofuran, and 1,4-dioxane.

The electrolyte solution of the present invention may be combined with a polymer material and thereby formed into a gel-like (plasticized), gel electrolyte solution.

Examples of such a polymer material include conventionally known polyethylene oxide, polypropylene oxide, modified products thereof (see JP H08-222270 A, JP 2002-100405 A); polyacrylate-based polymers, polyacrylonitrile, and fluororesins such as polyvinylidene fluoride and vinylidene fluoride-hexafluoropropylene copolymers (see JP H04-506726 T, JP H08-507407 T, JP H10-294131 A); composites of any of these fluororesins and any hydrocarbon resin (see JP H11-35765 A, JP H11-86630 A). In particular, polyvinylidene fluoride or a vinylidene fluoride-hexafluoropropylene copolymer is preferably used as a polymer material for gel electrolytes.

The electrolyte solution of the present invention may also contain an ion conductive compound disclosed in Japanese Patent Application No. 2004-301934.

This ion conductive compound is an amorphous fluoropolyether compound having a fluorine-containing group at a side chain and is represented by formula (1-1):

$$A\text{-}(D)\text{-}B \tag{1-1}$$

wherein D is represented by formula (2-1):

$$\text{-}(D1)_n\text{-}(FAE)_m\text{-}(AE)_p\text{-}(Y)_q\text{-} \tag{2-1}$$

wherein D1 is an ether unit having a fluoroether group at a side chain and is represented by formula (2a):

(2a)

wherein Rf is a fluoroether group optionally having a cross-linkable functional group; and $R^{10}$ is a group or a bond that links Rf and the main chain;

FAE is an ether unit having a fluorinated alkyl group at a side chain and is represented by formula (2b):

(2b)

wherein Rfa is a hydrogen atom or a fluorinated alkyl group optionally having a cross-linkable functional group; and $R^{11}$ is a group or a bond that links Rfa and the main chain;

AE is an ether unit represented by formula (2c):

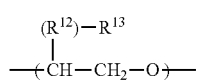

(2c)

wherein $R^{13}$ is a hydrogen atom, an alkyl group optionally having a cross-linkable functional group, an aliphatic cyclic hydrocarbon group optionally having a cross-linkable functional group, or an aromatic hydrocarbon group optionally having a cross-linkable functional group; and $R^{12}$ is a group or a bond that links $R^{13}$ and the main chain;

Y is a unit having at least one selected from formulas (2d-1) to (2d-3):

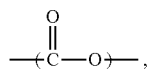

(2d-1)

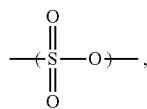

(2d-2)

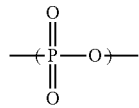

(2d-3)

wherein n is an integer of 0 to 200; m is an integer of 0 to 200; p is an integer of 0 to 10000; and q is an integer of 1 to 100, where n+m is not 0 and the bonding order of D1, FAE, AE, and Y is not specified); and A and B are the same as or different from each other and are each a hydrogen atom, an alkyl group optionally having a fluorine atom and/or a cross-linkable functional group, a phenyl group optionally having a fluorine atom and/or a cross-linkable functional group, a —COOH group, —OR (where R is a hydrogen atom or an alkyl group optionally having a fluorine atom and/or a cross-linkable functional group), an ester group, or a carbonate group (when an end of D is an oxygen atom, A and B each are none of a —COOH group, —OR, an ester group, and a carbonate group).

The electrolyte solution of the present invention may further contain any other additives, if necessary. Examples of such other additives include metal oxides and glass.

The electrolyte solution of the present invention may be prepared by any method using the aforementioned components.

The electrolyte solution of the present invention can be suitably applied to electrochemical devices such as lithium ion secondary batteries and electric double-layer capacitors. An electrochemical device including the electrolyte solution of the present invention is also provided according to one aspect of the present invention.

Examples of the electrochemical device include lithium ion secondary batteries, capacitors (electric double-layer capacitors), radical batteries, solar cells (in particular, dye-sensitized solar cells), fuel cells, various electrochemical sensors, electrochromic elements, electrochemical switching elements, aluminum electrolytic capacitors, and tantalum electrolytic capacitors. Preferred are lithium ion secondary batteries and electric double-layer capacitors.

A module including the above electrochemical device is also provided according to one aspect of the present invention.

The present invention also relates to a lithium ion secondary battery including the electrolyte solution of the present invention. The lithium ion secondary battery of the present invention includes a positive electrode, a negative electrode, and the aforementioned electrolyte solution.

<Negative Electrode>

First, a negative electrode active material used for the negative electrode is described. The negative electrode active material may be any material that can electrochemically occlude and release lithium ions. Specific examples thereof include carbonaceous materials, alloy materials, and lithium-containing metal oxide composite materials. These may be used alone or in any combination of two or more.

(Negative Electrode Active Material)

Examples of the negative electrode active material include carbonaceous materials, alloy materials, and lithium-containing metal oxide composite materials.

For a good balance between the initial irreversible capacity and the high-current-density charge and discharge characteristics, the carbonaceous materials to be used as negative electrode active materials are preferably selected from:

(1) natural graphite;

(2) carbonaceous materials obtained by one or more heat treatments of artificial carbonaceous substances or artificial graphite substances at 400° C. to 3200° C.;

(3) carbonaceous materials in which the negative electrode active material layer includes at least two or more carbonaceous matters having different crystallinities and/or has an interface between the carbonaceous matters having different crystallinities; and (4) carbonaceous materials in which the negative electrode active material layer includes at least two or more carbonaceous matters having different orientations and/or has an interface between the carbonaceous matters having different orientations. The carbonaceous materials (1) to (4) may be used alone or in any combination of two or more at any ratio.

Examples of the artificial carbonaceous substances and the artificial graphite substances of the above carbonaceous materials (2) include those prepared by covering the surface of natural graphite with coal-based coke, petroleum-based coke, coal-based pitch, petroleum-based pitch, or the like and then heating the covered surface, carbon materials prepared by graphitizing natural graphite and part or all of coal-based coke, petroleum-based coke, coal-based pitch, petroleum-based pitch, needle coke, and pitch coke, pyrolysates of organic matter such as furnace black, acetylene black, and pitch-based carbon fibers; carbonizable organic matter and carbides thereof; and solutions prepared by dissolving carbonizable organic matter in a low-molecular-weight organic solvent such as benzene, toluene, xylene, quinoline, or n-hexane, and carbides thereof.

The alloy materials to be used as negative electrode active materials may be any material that can occlude and release lithium, and examples thereof include simple lithium, simple metals and alloys that constitute lithium alloys, and compounds based thereon, such as oxides, carbides, nitrides, silicides, sulfides, and phosphides thereof. The simple metals and alloys constituting lithium alloys are preferably materials containing any of metal or semi-metal elements (i.e., excluding carbon) in the Groups 13 and 14, more preferably simple metal of aluminum, silicon, and tin (hereinafter, also referred to as "specific metal elements"), and alloys or compounds containing any of these atoms. These materials may be used alone or in combination of two or more at any ratio.

Examples of the negative electrode active material having at least one atom selected from the specific metal elements include simple metal of any one specific metal element, alloys of two or more specific metal elements, alloys of one or two or more specific metal elements and one or two or more other metal elements, compounds containing one or two or more specific metal elements, and composite compounds such as oxides, carbides, nitrides, silicides, sulfides, and phosphides of these compounds. Use of such a simple metal, alloy, or metal compound as the negative electrode active material can give a high capacity to batteries.

Examples thereof further include compounds in which any of the above composite compounds are complicatedly bonded with several elements such as simple metals, alloys, and non-metal elements. Specifically, in the case of silicon or tin, for example, an alloy of this element and a metal that does not serve as a negative electrode may be used. In the case of tin, for example, a composite compound including a combination of five or six elements, including tin, a metal (excluding silicon) that serves as a negative electrode, a metal that does not serve as a negative electrode, and a non-metal element, may be used.

In order to provide a high capacity per unit mass when formed into batteries, preferred among these negative electrode active materials are simple metal of any one specific metal element, an alloy of any two or more specific metal elements, and an oxide, carbide, or nitride of a specific metal element. In terms of good capacity per unit mass and small environmental load, simple metal, an alloy, oxide, carbide, or nitride of silicon and/or tin is particularly preferred.

The lithium-containing metal oxide composite materials to be used as negative electrode active materials may be any material that can occlude and release lithium. In terms of high-current-density charge and discharge characteristics, materials containing titanium and lithium are preferred, lithium-containing metal oxide composites containing titanium are more preferred, and oxide composites of lithium and titanium (hereinafter, also abbreviated as "lithium titanium oxide composites") are still more preferred. In other words, use of a spinel-structured lithium titanium oxide composites contained in the negative electrode active material for electrochemical devices is particularly preferred because such a compound markedly reduces the output resistance.

Also preferred are lithium titanium oxide composites in which the lithium and/or titanium are/is replaced by any other metal element such as at least one element selected from the group consisting of Na, K, Co, Al, Fe, Ti, Mg, Cr, Ga, Cu, Zn, and Nb.

In order to provide a stable structure in doping and dedoping lithium ions, the metal oxide is preferably a lithium titanium oxide composite represented by formula (J) wherein $0.7 \leq x \leq 1.5$, $1.5 \leq y \leq 2.3$, $0 \leq z \leq 1.6$:

$$Li_xTi_yM_zO_4 \tag{J}$$

wherein M is at least one element selected from the group consisting of Na, K, Co, Al, Fe, Ti, Mg, Cr, Ga, Cu, Zn, and Nb.

I order to achieve a good balance of the battery performance, particularly preferred compositions represented by formula (J) are those satisfying one of the following:
(a) $1.2 \leq x \leq 1.4$, $1.5 \leq y \leq 1.7$, $z=0$;
(b) $0.9 \leq x \leq 1.1$, $1.9 \leq y \leq 2.1$, $z=0$;
(c) $0.7 \leq x \leq 0.9$, $2.1 \leq y \leq 2.3$, $z=0$.

Particularly preferred representative compositions of the compound are $Li_{4/3}Ti_{5/3}O_4$, corresponding to the composition (a), $Li_1Ti_2O_4$, corresponding to the composition (b), and $Li_{4/5}Ti_{11/5}O_4$, corresponding to the composition (c).

Preferred examples of the structure satisfying $Z \neq 0$ include $Li_{4/3}Ti_{4/3}Al_{1/3}O_4$.

<Structure and Production Method of Negative Electrode>

The electrode can be produced by any known method that does not significantly impair the effects of the present invention. For example, the negative electrode may be produced by mixing a negative electrode active material with a binder (binding agent) and a solvent, and if necessary, a thickening agent, a conductive material, filler, and other components, to form slurry; applying this slurry to a current collector; drying the slurry; and pressing the workpiece.

In the case of an alloy material, one example of the production method is a method in which a thin film layer (negative electrode active material layer) containing the above negative electrode active material is produced by vapor deposition, sputtering, plating, or the like technique.

(Binding Agent)

The binder for binding the negative electrode active material may be any material that is stable against the electrolyte solution and a solvent to be used in the production of the electrode.

Specific examples thereof include resin polymers such as polyethylene, polypropylene, polyethylene terephthalate, polymethyl methacrylate, aromatic polyamide, polyimide, cellulose, and nitro cellulose; rubbery polymers such as styrene/butadiene rubber (SBR), polyisoprene rubber, polybutadiene rubber, fluororubber, acrylonitrile/butadiene rubber (NBR), and ethylene/propylene rubber; styrene/butadiene/styrene block copolymers and hydrogenated products thereof; thermoplastic elastomeric polymers such as ethylene/propylene/diene terpolymers (EPDM), styrene/ethylene/butadiene/styrene copolymers, styrene/isoprene/styrene block copolymers, and hydrogenated products thereof; soft resin polymers such as syndiotactic-1,2-polybutadiene, polyvinyl acetate, ethylene/vinyl acetate copolymers, and propylene/α-olefin copolymers; fluoropolymers such as polyvinylidene fluoride, polytetrafluoroethylene, fluorinated polyvinylidene fluoride, and tetrafluoroethylene/ethylene copolymers; and polymer compositions having an ion conductivity of alkali metal ions (especially, lithium ions). These agents may be used alone or in any combination of two or more at any ratio.

The proportion of the binder relative to the negative electrode active material is preferably 0.1% by mass or more, more preferably 0.5% by mass or more, particularly preferably 0.6% by mass or more, while it is preferably 20% by mass or less, more preferably 15% by mass or less, still more preferably 10% by mass or less, particularly preferably 8% by mass or less. If the proportion of the binder relative to the negative electrode active material exceeds the above range, a large proportion of the binder may fail to contribute to the battery capacity, so that the battery capacity may decrease. If the proportion thereof is lower than the above range, the resulting negative electrode may have lower strength.

In particular, in the case of using a rubbery polymer typified by SBR as a main component, the proportion of the binder relative to the negative electrode active material is usually 0.1% by mass or more, preferably 0.5% by mass or more, more preferably 0.6% by mass or more, while it is usually 5% by mass or less, preferably 3% by mass or less, more preferably 2% by mass or less. In the case of using a fluoropolymer typified by polyvinylidene fluoride as a main component, the proportion of the binder relative to the negative electrode active material is usually 1% by mass or more, preferably 2% by mass or more, more preferably 3% by mass or more, while it is usually 15% by mass or less, preferably 10% by mass or less, more preferably 8% by mass or less.

(Slurry-Forming Solvent)

A solvent for forming slurry may be any solvent that can dissolve or disperse the negative electrode active material and the binder, and a thickening agent and a conductive material that are used as necessary. The slurry-forming solvent may be either an aqueous solvent or an organic solvent.

Examples of the aqueous solvent include water and alcohols. Examples of the organic solvent include N-methylpyrrolidone (NMP), dimethyl formamide, dimethyl acetamide, methyl ethyl ketone, cyclohexanone, methyl acetate, methyl acrylate, diethyl triamine, N,N-dimethyl aminopropyl amine, tetrahydrofuran (THF), toluene, acetone, diethyl ether, dimethyl acetamide, hexamethyl phospharamide, dimethyl sulfoxide, benzene, xylene, quinoline, pyridine, methyl naphthalene, and hexane.

In particular, in the case of an aqueous solvent, preferably, the aqueous solvent is made to contain a component such as a dispersant corresponding to a thickening agent, and is formed into slurry using a latex such as SBR. These solvents may be used alone or in any combination of two or more at any ratio.

(Current Collector)

A current collector for holding the negative electrode active material may be any known one. Examples of the negative electrode current collector include metal materials such as aluminum, copper, nickel, stainless steel, and nickel-plated steel. In terms of easy processing and cost efficiency, copper is particularly preferred.

If the current collector is a metal material, the current collector may be in the form of, for example, metal foil, metal cylinder, metal coil, metal plate, metal film, expanded metal, punched metal, or metal foam. Preferred is a metal film, more preferred is copper foil, and still more preferred is rolled copper foil prepared by rolling or electrolyzed copper foil prepared by electrolysis. Each of these may be used as a current collector.

The current collector usually has a thickness of 1 μm or larger, preferably 5 μm or larger, while it is usually 100 μm or smaller, preferably 50 μm or smaller. Too thick a negative electrode current collector may cause an excessive decrease in capacity of the whole battery, whereas too thin a current collector may be difficult to handle.

(Ratio of Thicknesses Between Current Collector and Negative Electrode Active Material Layer)

The ratio of thickness between the current collector and the negative electrode active material layer may be any value, and the value "(thickness of negative electrode active material layer on one side immediately before filling of electrolyte solution)/(thickness of current collector)" is preferably 150 or smaller, still more preferably 20 or smaller, particularly preferably 10 or smaller, while it is preferably 0.1 or greater, still more preferably 0.4 or greater, particularly preferably 1 or greater. If the ratio between the thicknesses of the current collector and the negative electrode active material layer exceeds the above range, the current collector may generate heat due to Joule heat during high-current-density charge and discharge. If the ratio is below the above range, the volume proportion of the current collector to the negative electrode active material is high, so that the battery capacity may be low.

<Positive Electrode>

(Positive Electrode Active Material)

A positive electrode active material used for the positive electrode is described below. The positive electrode active material used in the present invention is preferably a lithium transition metal compound powder that can intercalate and release lithium ions and that satisfies one of the following three conditions:

1. a lithium transition metal compound powder having a pH of 10.8 or higher;
2. a lithium transition metal compound powder containing a compound having at least one or more elements selected from Mo, W, Nb, Ta, and Re and a compound having a B element and/or a Bi element; and
3. a lithium transition metal compound powder having a peak within a pore radius range of not smaller than 80 nm but smaller than 800 nm.

(Lithium Transition Metal Compound)

The lithium transition metal compound is a compound having a structure that can release and intercalate Li ions, and examples thereof include sulfides, phosphate compounds, and lithium transition metal oxide composites. Examples of the sulfides include compounds having a two-dimensional lamellar structure such as $TiS_2$ and $MoS_2$ and chevrel compounds having a firm three-dimensional skeleton structure represented by $Me_xMo_6S_8$ wherein Me is a transition metal such as Pb, Ag, or Cu. Examples of the phosphate compounds include those having an olivine structure generally represented by $LiMePO_4$ wherein Me is at least one or more transition metals. Specific examples thereof include $LiFePO_4$, $LiCoPO_4$, $LiNiPO_4$, and $LiMnPO_4$. Examples of the lithium transition metal oxide composites include those having a three-dimensionally diffusible spinel structure and those having a lamellar structure that enables two-dimensional diffusion of lithium ions. Those having a spinel structure are generally represented by $LiMe_2O_4$ wherein Me is at least one transition metal. Specific examples thereof include $LiMn_2O_4$, $LiCoMnO_4$, $LiNi_{0.5}Mn_{1.5}O_4$, and $LiCoVO_4$. Those having a lamellar structure are generally represented by $LiMeO_2$ wherein Me is at least one transition metal. Specific examples thereof include $LiCoO_2$, $LiNiO_2$, $LiNi_{1-x}Co_xO_2$, $LiNi_{1-x-y}Co_xMn_yO_2$, $LiNi_{0.5}Mn_{0.5}O_2$, $Li_{1.2}Cr_{0.4}Mn_{0.4}O_2$, $Li_{1.2}Cr_{0.4}Ti_{0.4}O_2$, and $LiMnO_2$.

Particularly preferred is a lithium nickel manganese cobalt oxide composite or $LiCoO_2$.

In terms of good diffusion of lithium ions, the lithium transition metal compound powder preferably has an olivine structure, a spinel structure, or a lamellar structure. Particularly preferred is one having a lamellar structure.

The lithium transition metal compound powder may include any additional element. The additional element is one or more selected from B, Na, Mg, Al, K, Ca, Ti, V, Cr, Fe, Cu, Zn, Sr, Y, Zr, Nb, Ru, Rh, Pd, Ag, In, Sb, Te, Ba, Ta, Mo, W, Re, Os, Ir, Pt, Au, Pb, La, Ce, Pr, Nd, Sm, Eu, Gd, Tb, Dy, Ho, Er, Tm, Yb, Lu, Bi, N, F, S, Cl, Br, and I. These additional elements may be introduced into the crystal structure of the lithium nickel manganese cobalt oxide composite, or may not be introduced into the crystal structure of the lithium nickel manganese cobalt oxide composite but be unevenly distributed as simple substances or compounds on surfaces or grain boundaries of the particles.

(Additives)

In the present invention, a compound (hereinafter, also referred to as an "additive 1") having at least one or more elements selected from Mo, W, Nb, Ta, and Re (hereinafter, also referred to as "additive elements 1") and a compound (hereinafter, also referred to as an "additive 2") having at least one element selected from B and Bi (hereinafter, also referred to as additive elements 2") may be used.

In order to provide a significant effect, Mo or W is preferred, and W is most preferred, among these additive elements 1. Further, B is preferred among these additive elements 2 because B is inexpensively available as an industrial material and is a light element.

The compound (additive 1) having an additive element 1 may be of any type that leads to the effects of the present invention, and is usually an oxide.

Examples of the additive 1 include MoO, $MoO_2$, $MoO_3$, $MoO_x$, $Mo_2O_3$, $Mo_2O_5$, $Li_2MoO_4$, WO, $WO_2$, $WO_3$, $WO_x$, $W_2O_3$, $W_2O_5$, $W_{18}O_{49}$, $W_{20}O_{58}$, $W_{24}O_{70}$, $W_{25}O_{73}$, $W_{40}O_{118}$, $Li_2WO_4$, NbO, $NbO_2$, $Nb_2O_3$, $Nb_2O_5$, $Nb_2O_5 \cdot nH_2O$, $LiNbO_3$, $Ta_2O$, $Ta_2O_5$, $LiTaO_3$, $ReO_2$, $ReO_3$, $Re_2O_3$, and $Re_2O_7$. Preferred are $MoO_3$, $Li_2MoO_4$, $WO_3$, and $Li_2WO_4$, and particularly preferred is $WO_3$, because they are relatively easily available as industrial materials or they contain lithium. These additives 1 may be used alone or in combination of two or more.

The compound (additive 2) having an additive element 2 may be of any type that leads to the effects of the present invention, and is usually boric acid, a salt of an oxoacid, an oxide, or a hydroxide. Preferred among these additives 2 are boric acid and oxides, and particularly preferred is boric acid, because they are inexpensively available as industrial materials.

Examples of the additive 2 include BO, $B_2O_2$, $B_2O_3$, $B_4O_5$, $B_6O$, $B_7O$, $B_{13}O_2$, $LiBO_2$, $LiB_5O_8$, $Li_2B_4O_7$, $HBO_2$, $H_3BO_3$, $B(OH)_3$, $B(OH)_4$, $BiBO_3$, $Bi_2O_3$, $Bi_2O_5$, and $Bi(OH)_3$. Preferred are $B_2O_3$, $H_3BO_3$, and $Bi_2O_3$, and particularly preferred is $H_3BO_3$, because they are relatively inexpensively and easily available as industrial materials. These additives 2 may be used alone or in combination of two or more.

With respect to the sum of the amounts of the additive 1 and the additive 2 relative to the total molar amount of the transition metal elements constituting the main components, the lower limit thereof is usually 0.1 mol % or more, preferably 0.3 mol % or more, more preferably 0.5 mol % or more, particularly preferably 1.0 mol % or more, whereas the upper limit thereof is usually less than 8 mol %, preferably 5 mol % or less, more preferably 4 mol % or less, particularly preferably 3 mol % or less. If the sum of the amounts thereof is below the lower limit, the effects of the additives may not be possibly achieved. If the sum of the amounts thereof exceeds the upper limit, the battery performance may possibly be impaired.

(Production Method of Positive Electrode Active Material)

The positive electrode active material may be produced by any usual method of producing inorganic compounds. In particular, various methods may be mentioned for producing a spherical or ellipsoidal active material. For example, a material substance of transition metal is dissolved or pulverized and dispersed in a solvent such as water, and the pH of the solution or dispersion is adjusted under stirring to form a spherical precursor. The precursor is recovered and, if necessary, dried. Then, a Li source such as LiOH, $Li_2CO_3$, or $LiNO_3$ is added thereto and the mixture is sintered at high temperature, thereby providing an active material.

In order to produce a positive electrode, the aforementioned positive electrode active materials may be used alone or in any combination of two or more having different compositions at any ratio. Preferred examples of the combination in this case include a combination of $LiCoO_2$ and $LiMn_2O_4$ in which Mn is partially replaced by different transition metal(s) (e.g., $LiNi_{0.33}Co_{0.33}Mn_{0.33}O_2$), and a combination of $LiCoO_2$ and $LiCoO_2$ in which Co is partially replaced by different transition metal(s).

(Production Method of Lithium Transition Metal Compound Powder)

The lithium transition metal compound powder may be produced by any method, and may be suitably produced by a production method including: pulverizing and uniformly dispersing a lithium compound, at least one transition metal compound selected from Mn, Co, and Ni, and the aforementioned additive(s) in a liquid medium to provide slurry; spray-drying the resulting slurry; and sintering the resulting spray-dried matter.

For example, in the case of a lithium nickel manganese cobalt oxide composite powder, such a powder can be produced by dispersing a lithium compound, a nickel compound, a manganese compound, a cobalt compound, and the aforementioned additive(s) in a liquid medium to provide slurry, spray-drying the slurry, and sintering the resulting spray-dried matter in an oxygen-containing gas atmosphere.

The following will specifically describe the method of producing a lithium transition metal compound powder by taking, as an example, a production method for a lithium nickel manganese cobalt oxide composite powder that is one preferred embodiment of the present invention.

I) Slurry Preparation Step

In the production of the lithium transition metal compound powder, examples of the lithium compound among the material compounds used in the slurry preparation include $Li_2CO_3$, $LiNO_3$, $LiNO_2$, LiOH, $LiOH \cdot H_2O$, LiH, LiF, LiCl, LiBr, LiI, $CH_3OOLi$, $Li_2O$, $Li_2SO_4$, Li dicarboxylate, Li citrate, fatty acid Li, and alkyllithiums. Preferred among these lithium compounds are lithium compounds free from a nitrogen atom, a sulfur atom, and a halogen atom because they do not generate hazardous materials such as $SO_X$ and $NO_X$ in the sintering step, and compounds that are likely to form voids in the secondary particles of the spray-dried powder by, for example, generating decomposed gas during sintering. In consideration of these points, $Li_2CO_3$, LiOH, and $LiOH \cdot H_2O$ are preferred, and $Li_2CO_3$ is particularly preferred. These lithium compounds may be used alone or in combination of two or more.

Examples of the nickel compound include $Ni(OH)_2$, NiO, NiOOH, $NiCO_3$, $2NiCO_3 \cdot 3Ni(OH)_2 \cdot 4H_2O$, $NiC_2O_4 \cdot 2H_2O$, $Ni(NO_3)_2 \cdot 6H_2O$, $NiSO_4$, $NiSO_4 \cdot 6H_2O$, fatty acid nickel, and nickel halides. Preferred are nickel compounds such as $Ni(OH)_2$, NiO, NiOOH, $NiCO_3$, $2NiCO_3 \cdot 3Ni(OH)_2 \cdot 4H_2O$, and $NiC_2O_4 \cdot 2H_2O$ because they do not generate hazardous materials such as $SO_X$ and $NO_X$ in the sintering step. Particularly preferred are $Ni(OH)_2$, NiO, NiOOH, and $NiCO_3$ because they are inexpensively available as industrial materials and have high reactivity, and also particularly preferred are $Ni(OH)_2$, NiOOH, and $NiCO_3$ because they are likely to form voids in the secondary particles of the spray-dried powder by, for example, generating decomposed gas during sintering. These nickel compounds may be used alone or in combination of two or more.

Examples of the manganese compound include manganese oxides such as $Mn_2O_3$, $MnO_2$, and $Mn_3O_4$, manganese salts such as $MnCO_3$, $Mn(NO_3)_2$, $MnSO_4$, manganese acetate, manganese dicarboxylates, manganese citrate, and fatty acid manganese, oxyhydroxides, and halides such as manganese chloride. Preferred among these manganese compounds are $MnO_2$, $Mn_2O_3$, $Mn_3O_4$, and $MnCO_3$ because they do not generate gas such as $SO_X$ and $NO_X$ in the sintering step and are inexpensively available as industrial materials. These manganese compounds may be used alone or in combination of two or more.

Examples of the cobalt compound include $Co(OH)_2$, CoOOH, CoO, $Co_2O_3$, $Co_3O_4$, $Co(OCOCH_3)_2 \cdot 4H_2O$, $CoCl_2$, $Co(NO_3)_2 \cdot 6H_2O$, $Co(SO_4)_2 \cdot 7H_2O$, and $CoCO_3$. Preferred among these are $Co(OH)_2$, CoOOH, CoO, $Co_2O_3$, $Co_3O_4$, and $CoCO_3$ because they do not generate hazardous materials such as $SO_X$ and $NO_X$ in the sintering step. Still more preferred are $Co(OH)_2$ and CoOOH because they are industrially inexpensively available and have high reactivity. In addition, particularly preferred are $Co(OH)_2$, CoOOH, and $CoCO_3$ because they are likely to form voids in the secondary particles of the spray-dried powder by, for example, generating decomposed gas during sintering. These cobalt compounds may be used alone or in combination of two or more.

In addition to the above Li, Ni, Mn, and Co material compounds, the aforementioned additional elements may be introduced by element replacement, or any compound group may be used for the purpose of efficiently forming voids in the secondary particles formed by spray-drying to be mentioned later. The compound to be used for efficiently forming voids in the secondary particles may be added at any stage, and may be added before or after the mixing of the materials in accordance with the properties thereof. In particular, a compound that is likely to be decomposed in the mixing step due to mechanical shearing force is preferably added after the mixing step. The additive(s) is/are as mentioned above.

The materials may be mixed by any method. Either a wet method or a dry method may be employed. Examples thereof include methods using a device such as a ball mill, a vibrating mill, or a bead mill. Wet mixing in which the material compounds are mixed in a liquid medium such as water or alcohol is preferred because the materials can be more uniformly mixed and the reactivity of the mixture in the sintering step can be improved.

The mixing time may vary in accordance with the mixing method and may be any period of time as long as the materials are uniformly mixed in the order of the particle level. For example, the mixing time is usually about one hour to two days in the case of using a ball mill (wet or dry method), and the residence time is usually about 0.1 hours to 6 hours in the case of using a bead mill (continual wet method).

In the stage of mixing the materials, the materials are preferably simultaneously pulverized. The degree of pulverization is indicated by the particle size of the pulverized particles of the materials, and the average particle size (median size) is usually 0.6 μm or smaller, preferably 0.55 μm or smaller, still more preferably 0.52 μm or smaller, most preferably 0.5 μm or smaller. Too large an average particle size of the pulverized particles of the materials may lead to low reactivity in the sintering step and difficulty in making the composition uniform. In contrast, pulverizing the materials into excessively small particles may cost high. Thus, the materials have only to be pulverized into particles usually having an average particle size of 0.01 μm or greater, preferably 0.02 μm or greater, still more preferably 0.05 μm or greater. Such a degree of pulverization may be achieved by any means, and wet pulverization is preferred. One specific example thereof is dyno-mill.

The median size of the pulverized particles in the slurry is determined with a known laser diffraction/scattering particle size distribution analyzer at a refractive index of 1.24, the particle size being based on volume. The dispersion medium used in the measurement is a 0.1 wt % sodium hexametaphosphate aqueous solution, and the measurement was performed after a five-minute ultrasonic dispersion (output: 30 W; frequency: 22.5 kHz).

II) Spray-Drying Step

The wet mixing is usually followed by a drying step. The drying may be performed by any method. Spray drying is preferred in terms of uniformity of generated particulates, powder flowability, and powder handleability, and efficient production of dried particles.

(Spray-Dried Powder)

In the method of producing a lithium transition metal compound powder such as the above lithium nickel manganese cobalt oxide composite powder, the slurry obtained by wet-pulverizing the material compounds and the aforementioned additive(s) is spray-dried, so that the primary particles coagulate to form secondary particles, resulting in the target powder. The geometric features of the spray-dried powder formed by coagulation of the primary particles into the secondary particles may be analyzed by, for example, SEM observation or cross-sectional SEM observation.

III) Sintering Step

The spray-dried powder obtained in the above spray-drying step is then subjected to a sintering treatment as a sintering precursor.

The sintering conditions depend on the composition and the lithium compound material used. Still, too high a sintering temperature tends to cause excessive growth of the primary particles, excessive sintering of the particles, and too small a specific surface area of the particles. In contrast, too low a sintering temperature tends to cause mixing of hetero-phases and non-growth of the crystal structure, resulting in an increase in lattice strain. Further, the specific surface area tends to be too large. The sintering temperature is usually 1000° C. or higher, preferably 1010° C. or higher, more preferably 1025° C. or higher, most preferably 1050° C. or higher, while it is preferably 1250° C. or lower, more preferably 1200° C. or lower, still more preferably 1175° C. or lower.

The sintering may be performed in, for example, a box furnace, a tube furnace, a tunnel furnace, or a rotary kiln. The sintering step is usually divided into three sections, i.e., a temperature-increasing section, a maximum-temperature-keeping section, and a temperature-decreasing section. The second, maximum-temperature-keeping section is not necessarily performed only once, and may be performed twice or more in accordance with the purpose. The step consisting of the temperature-increasing section, the maximum-temperature-keeping section, and the temperature-decreasing section may be repeated twice or more times while a separating step in which the coagulated secondary particles are separated without destruction of the particles, or a pulverizing step in which the coagulated secondary particles are pulverized into the primary particles or much smaller particles is performed between the respective sintering steps.

In the case of two-stage sintering, the temperature in the first stage is preferably kept at a temperature of not lower than the temperature where the Li material starts to decompose but not higher than the temperature where the Li material melts. For example, in the case of using lithium carbonate, the temperature kept in the first stage is preferably 400° C. or higher, more preferably 450° C. or higher, still more preferably 500° C. or higher, most preferably 550° C. or higher, while it is usually 950° C. or lower, more preferably 900° C. or lower, still more preferably 880° C. or lower, most preferably 850° C. or lower.

In the temperature-increasing section that leads to the maximum-temperature-keeping section, the temperature inside the furnace is usually increased at a temperature-increasing rate of 1° C./min or higher and 20° C./min or lower. Too low a temperature-increasing rate is industrially disadvantageous because the section takes too long a time, but too high a temperature-increasing rate is also not preferred because the temperature inside the furnace fails to follow the set temperature in some furnaces. The temperature-increasing rate is preferably 2° C./min or higher, more preferably 3° C./min or higher, while it is preferably 18° C./min or lower, more preferably 15° C./min or lower.

The temperature-keeping time in the maximum-temperature-keeping section varies in accordance with the set temperature. If the temperature is within the above range, the temperature-keeping time is usually 15 minutes or longer, preferably 30 minutes or longer, still more preferably 45 minutes or longer, most preferably 1 hour or longer, while it is usually 24 hours or shorter, preferably 12 hours or shorter, still more preferably 9 hours or shorter, most preferably 6 hours or shorter. Too short a sintering time may fail to provide a lithium transition metal compound powder with good crystallinity. Too long a sintering time is not practical. Too long a sintering time disadvantageously requires post-separation or makes it difficult to perform such post-separation.

In the temperature-decreasing section, the temperature inside the furnace is usually decreased at a temperature-decreasing rate of 0.1° C./min or higher and 20° C./min or lower. Too low a temperature-decreasing rate is industrially disadvantageous because the section takes too long a time, but too high a temperature-decreasing rate tends to cause insufficient uniformity of the target matter or rapid deterioration of the container. The temperature-decreasing rate is preferably 1° C./min or higher, more preferably 3° C./min or higher, while it is preferably 15° C./min or lower.

An appropriate oxygen partial pressure region varies in accordance with the target composition of a lithium transition metal compound powder. Thus, the sintering atmosphere is any appropriate gas atmosphere satisfying the appropriate oxygen partial pressure region. Examples of the atmospheric gas include oxygen, the air, nitrogen, argon, hydrogen, carbon dioxide, and mixtures of any of these gases. For the lithium nickel manganese cobalt oxide composite powder, an oxygen-containing gas atmosphere, such as the air, may be used. The oxygen concentration in the atmosphere is usually 1 vol % or more, preferably 10 vol % or more, more preferably 15 vol % or more, while it is usually 100 vol % or less, preferably 50 vol % or less, more preferably 25 vol % or less.

In the production of a lithium transition metal compound powder, such as a lithium nickel manganese cobalt oxide composite powder having the above specific composition, by the aforementioned production method under constant production conditions, the molar ratio of Li/Ni/Mn/Co in the target powder can be controlled by adjusting the ratio of mixing the compounds in preparation of slurry containing a lithium compound, a nickel compound, a manganese compound, and a cobalt compound, and an additive(s) dispersed in a liquid medium.

The lithium transition metal compound powder, such as a lithium nickel manganese cobalt oxide composite powder, thus obtained can provide a positive electrode material for lithium ion secondary batteries having well-balanced performance, i.e., having a high capacity and excellent low-temperature output characteristics and storage characteristics.

<Structure and Production Method of Positive Electrode>

The following gives the structure of the positive electrode. The positive electrode may be produced by forming a positive electrode active material layer containing a positive electrode active material and a binding agent on a current collector. The production of a positive electrode with a positive electrode active material may be performed by a usual method. Specifically, a positive electrode active material and a binding agent, and if necessary, other components such as a conductive material and a thickening agent are dry-mixed to provide a sheet, and then this sheet is press-bonded to a positive electrode current collector, or these materials are dissolved or dispersed in a liquid medium to provide slurry, and then this slurry is applied to a positive electrode current collector and dried, so that a positive electrode active material layer is formed on the current collector. Thereby, a positive electrode is obtained.

The amount of the positive electrode active material in the positive electrode active material layer is preferably 80% by mass or more, more preferably 82% by mass or more, particularly preferably 84% by mass or more. The upper limit thereof is preferably 99% by mass, more preferably 98% by mass. Too small an amount of the positive electrode active material in the positive electrode active material layer may lead to an insufficient electric capacity. In contrast, too large an amount thereof may lead to an insufficient strength of the positive electrode.

(Binding Agent)

The binding agent used in the production of the positive electrode active material layer may be any binding agent. In the case of the applying technique, the binding agent has only to be a material that is to be dissolved or dispersed in a liquid medium used in the production of the electrode. Specific examples thereof include the same binding agents as those to be used in the above production of the negative electrode. These materials may be used alone or in any combination of two or more at any ratio.

The proportion of the binding agent in the positive electrode active material layer is usually 0.1% by mass or more, preferably 1% by mass or more, more preferably 1.5% by mass or more, while it is usually 80% by mass or less, preferably 60% by mass or less, still more preferably 40% by mass or less, most preferably 10% by mass or less. Too low a proportion of the binding agent may fail to sufficiently hold the positive electrode active material, so that the resulting positive electrode may have an insufficient mechanical strength, resulting in poor battery performance such as cycle characteristics. In contrast, too high a proportion thereof may lead to a decrease in battery capacity and conductivity.

(Slurry-Forming Solvent)

A solvent for forming slurry may be any solvent that can dissolve or disperse the positive electrode active material, the conductive material, and the binding agent, and a thickening agent that is used as necessary. The slurry-forming solvent may be either an aqueous solvent or an organic solvent. Examples of the aqueous medium include water and solvent mixtures of an alcohol and water. Examples of the organic medium include aliphatic hydrocarbons such as hexane; aromatic hydrocarbons such as benzene, toluene, xylene, and methyl naphthalene; heterocyclic compounds such as quinoline and pyridine; ketones such as acetone, methyl ethyl ketone, and cyclohexanone; esters such as methyl acetate and methyl acrylate; amines such as diethylene triamine and N,N-dimethylaminopropylamine; ethers such as diethyl ether, propylene oxide, and tetrahydrofuran (THF); amides such as N-methylpyrrolidone (NMP), dimethyl formamide, and dimethyl acetamide; and aprotic polar solvents such as hexamethyl phosphoramide and dimethyl sulfoxide.

(Current Collector)

A positive electrode current collector may be formed from any material, and any known material may be used. Specific examples thereof include metal materials such as aluminum, stainless steel, nickel-plated metals, titanium, and tantalum; and carbon materials such as carbon cloth and carbon paper. Preferred is any metal material, in particular aluminum.

In the case of a metal material, the current collector may be in the form of, for example, metal foil, metal cylinder, metal coil, metal plate, metal film, expanded metal, punched metal, or metal foam. In the case of a carbon material, the current collector may be in the form of, for example, carbon plate, carbon film, or carbon cylinder.

In order to decrease the electric contact resistance between the current collector and the positive electrode active material layer, a conductive assistant may also preferably be applied to a surface of the current collector. Examples of the conductive assistant include carbon and noble metals such as gold, platinum, and silver.

The ratio between the thicknesses of the current collector and the positive electrode active material layer may be any value, and the value "(thickness of positive electrode active material layer on one side immediately before filling of electrolyte solution)/(thickness of current collector)" is preferably 20 or smaller, more preferably 15 or smaller, most preferably 10 or smaller. The lower limit thereof is also preferably 0.5, more preferably 0.8, most preferably 1. If the ratio exceeds this range, the current collector may generate heat due to Joule heat during high-current-density charge and discharge. If the ratio is below the above range, the volume ratio of the current collector to the positive electrode active material is high, so that the battery capacity may be low.

<Separator>

In order to prevent a short circuit, a separator is usually disposed between the positive electrode and the negative electrode. In this case, the electrolyte solution of the present invention is usually impregnated into this separator.

The separator may be formed from any known material and may have any known shape as long as the effects of the present invention are not significantly impaired. The separator is preferably formed from a material stable to the electrolyte solution of the present invention, such as resin, glass fiber, or inorganic matter, and in the form of a porous sheet or a nonwoven fabric which are excellent in a liquid-retaining ability.

Examples of the material of a resin or glass-fiber separator include polyolefins such as polyethylene and polypropylene, aromatic polyamide, polytetrafluoroethylene, polyether sulfone, and glass filters. Particularly preferred are glass filter and polyolefins, still more preferred are polyolefins. These materials may be used alone or in any combination of two or more at any ratio.

The separator may have any thickness, and the thickness is usually 1 μm or larger, preferably 5 μm or larger, more preferably 8 μm or larger, while it is usually 50 μm or smaller, preferably 40 μm or smaller, more preferably 30 μm or smaller. The separator thinner than the above range may have poor insulation and poor mechanical strength. The separator thicker than the above range may lead to not only poor battery performance, such as rate characteristics, but also a low energy density of the whole electrochemical device.

If the separator is a porous one such as a porous sheet or a nonwoven fabric, the separator may have any porosity. The porosity is usually 20% or higher, preferably 35% or higher, more preferably 45% or higher, whereas the porosity is usually 90% or lower, preferably 85% or lower, more preferably 75% or lower. The separator having a porosity of lower than the above range tends to cause a high film resistance and poor rate characteristics. The separator having a porosity of higher than the above range tends to have a low mechanical strength and poor insulation.

The separator may also have any average pore size. The average pore size is usually 0.5 μm or smaller, preferably 0.2 μm or smaller, while it is usually 0.05 μm or larger. The separator having an average pore size exceeding the above range may easily cause a short circuit. The separator having an average pore size of lower than the above range may have a high film resistance and lead to poor rate characteristics.

Examples of the inorganic matter include oxides such as alumina and silicon dioxide, nitrides such as aluminum nitride and silicon nitride, and sulfates such as barium sulfate and calcium sulfate. The inorganic matter is in the form of particles or fibers.

The separator is in the form of a thin film such as a nonwoven fabric, a woven fabric, or a microporous film. The thin film favorably has a pore size of 0.01 to 1 μm and a thickness of 5 to 50 μm. Instead of the above independent thin film, the separator may have a structure in which a composite porous layer containing particles of the above inorganic matter is disposed on a surface of one or both of the positive and negative electrodes using a resin binding agent. For example, alumina particles having a 90% particle size of smaller than 1 μm are applied to both surfaces of the positive electrode with fluororesin used as a binding agent to form a porous layer.

The following will describe the battery design.

<Electrode Group>

The electrode group may be either a laminated structure including the above positive and negative electrode plates with the above separator in between, or a wound structure including the above positive and negative electrode plates in spiral with the above separator in between. The proportion of the volume of the electrode group in the battery internal volume (hereinafter, referred to as an electrode group occupancy) is usually 40% or higher, preferably 50% or higher, while it is usually 90% or lower, preferably 80% or lower.

The electrode group occupancy of lower than the above range may lead to a low battery capacity. The electrode group occupancy exceeding the above range may lead to small space for voids. Thus, when the battery temperature rises to high temperature, the components may expand or the liquid fraction of the electrolyte may show a high vapor pressure, so that the internal pressure may rise. As a result, the battery characteristics such as charge and discharge repeatability and the high-temperature storage characteristics may be impaired, and a gas-releasing valve for releasing the internal pressure toward the outside may work.

<Current-Collecting Structure>

The current-collecting structure may be any structure. In order to more effectively improve the high-current-density charge and discharge characteristics by the electrolyte solution of the present invention, the current-collecting structure is preferably a structure which has low resistances at wiring portions and jointing portions. With such low internal resistances, the effects of using the electrolyte solution of the present invention can particularly favorably be achieved.

In an electrode group having the layered structure, the metal core portions of the respective electrode layers are preferably bundled and welded to a terminal. If the area of a single electrode is large, the internal resistance is high. Thus, multiple terminals may preferably be formed in the electrode to decrease the resistance. In an electrode group having the wound structure, multiple lead structures may be disposed on each of the positive electrode and the negative electrode and bundled to a terminal. Thereby, the internal resistance can be decreased.

<External Case>

The external case may be made of any material that is stable to an electrolyte solution to be used. Specific examples thereof include metals such as nickel-plated steel plates, stainless steel, aluminum and aluminum alloys, and magnesium alloys, and a layered film (laminate film) of resin and aluminum foil. In terms of weight reduction, a metal such as aluminum or an aluminum alloy or a laminate film is favorably used.

External cases made of metal may have a sealed-up structure formed by welding the metal by laser welding, resistance welding, or ultrasonic welding or a caulking structure using the metal via a resin gasket. External cases made of a laminate film may have a sealed-up structure formed by hot melting the resin layers. In order to improve the sealability, a resin which is different from the resin of the laminate film may be disposed between the resin layers. Especially, in the case of forming a sealed-up structure by heat melting the resin layers via current collecting terminals, metal and resin are to be bonded. Thus, the resin to be disposed between the resin layers is favorably a resin having a polar group or a modified resin having a polar group introduced thereinto.

<Protective Element>

Any of positive temperature coefficient (PTC) thermistors the resistance of which increases in case of abnormal heating or excessive current flow, thermal fuses, thermistors, and valves (current-breaking valves) that break the current flowing in a circuit in response to a rapid increase in pressure or temperature inside the battery in case of abnormal heating may be used as a protective element. The protective element is preferably selected from elements that do not work under normal use at high currents. The battery is more preferably designed so as to cause neither abnormal heating nor thermal runaway even without a protective element.

<External Housing>

The electrochemical device of the present invention usually includes the electrolyte solution, the negative electrode, the positive electrode, the separator, and other components contained in an external housing. This external housing may be any known housing as long as the effects of the present invention are not significantly impaired. Specifically, the external housing may be formed of any material, and is usually formed of, for example, nickel-plated iron, stainless steel, aluminum or alloy thereof, nickel, or titanium.

The external housing may be in any form, and may be in the form of a cylinder, a square, a laminate, a coin, or a large size, for example. The shapes and the structures of the positive electrode, the negative electrode, and the separator may be changed in accordance with the shape of the battery.

The electrolyte solution of the present invention is especially useful as an electrolyte solution for electrochemical devices such as large-size lithium ion secondary batteries for hybrid vehicles or distributed generation, as well as useful as an electrolyte solution for electrochemical devices such as small-size lithium ion secondary batteries. A module including the lithium ion secondary battery of the present invention is also provided according to one aspect of the present invention.

The present invention also relates to an electric double-layer capacitor including a positive electrode, a negative electrode, and the aforementioned electrolyte solution.

In the electric double-layer capacitor of the present invention, at least one of the positive electrode and the negative electrode is a polarizable electrode. Examples of the polarizable electrode and a non-polarizable electrode include the following electrodes specifically disclosed in JP H09-7896 A.

The polarizable electrode mainly containing activated carbon used in the present invention is preferably one containing inactivated carbon having a large specific surface area and a conductive material, such as carbon black, providing electronic conductivity. The polarizable electrode can be formed by any of various methods. For example, a polarizable electrode containing activated carbon and carbon black can be produced by mixing activated carbon powder, carbon black, and phenolic resin, press-molding the mixture, and then firing and activating the mixture in an inert gas atmosphere and water vapor atmosphere. Preferably, this polarizable electrode is bonded to a current collector using a conductive adhesive, for example.

Alternatively, a polarizable electrode can also be formed by kneading activated carbon powder, carbon black, and a binder in the presence of alcohol and forming the mixture into a sheet shape, and then drying the sheet. This binder may be polytetrafluoroethylene, for example. Alternatively, a polarizable electrode integrated with a current collector can be produced by mixing activated carbon powder, carbon black, a binder, and a solvent to form slurry, and applying this slurry to metal foil of a current collector, and then drying the slurry.

The electric double-layer capacitor may have polarizable electrodes mainly containing activated carbon on the respective sides. Still, the electric double-layer capacitor may have a non-polarizable electrode on one side, for example, a positive electrode mainly containing an electrode active material such as a metal oxide and a negative electrode which is a polarizable electrode mainly containing activated carbon may be combined; or a negative electrode mainly containing a carbon material that can reversibly occlude and release lithium ions or a negative electrode of lithium metal or lithium alloy and a polarizable positive electrode mainly containing activated carbon may be combined.

In place of or in combination with activated carbon, any carbonaceous material such as carbon black, graphite, expanded graphite, porous carbon, carbon nanotube, carbon nanohorn, and Ketjenblack may be used.

The non-polarizable electrode is preferably an electrode mainly containing a carbon material that can reversibly occlude and release lithium ions, and this carbon material is made to occlude lithium ions in advance. In this case, the electrolyte used is a lithium salt. The electric double-layer capacitor having such a structure can achieve a much higher withstand voltage exceeding 4 V.

The solvent used in preparation of slurry in the production of electrodes is preferably one that dissolves a binder. In accordance with the type of a binder, N-methylpyrrolidone, dimethyl formamide, toluene, xylene, isophorone, methyl ethyl ketone, ethyl acetate, methyl acetate, dimethyl phthalate, ethanol, methanol, butanol, or water is appropriately selected.

Examples of the activated carbon used for the polarizable electrode include phenol resin-type activated carbon, coconut shell-type activated carbon, and petroleum coke-type activated carbon. In order to achieve a large capacity, petroleum coke-type activated carbon or phenol resin-type activated carbon is preferably used. Examples of methods of activating the activated carbon include steam activation and molten KOH activation. In order to achieve a larger capacity, activated carbon prepared by molten KOH activation is preferably used.

Preferred examples of the conductive material used for the polarizable electrode include carbon black, Ketjenblack, acetylene black, natural graphite, artificial graphite, metal fiber, conductive titanium oxide, and ruthenium oxide. In order to achieve good conductivity (i.e., low internal resistance), and because too large an amount thereof may lead to a decreased capacity of the product, the amount of the conductive material such as carbon black used for the polarizable electrode is preferably 1 to 50% by mass in the sum of the amounts of the activated carbon and the conductive material.

In order to provide an electric double-layer capacitor having a large capacity and a low internal resistance, the activated carbon used for the polarizable electrode preferably has an average particle size of 20 μm or smaller and a specific surface area of 1500 to 3000 m$^2$/g. Preferred examples of the carbon material for providing an electrode mainly containing a carbon material that can reversibly occlude and release lithium ions include natural graphite, artificial graphite, graphitized mesocarbon microsphere, graphitized whisker, vapor-grown carbon fiber, sintered furfuryl alcohol resin, and sintered novolak resin.

The current collector may be any chemically and electrochemically corrosion-resistant one. Preferred examples of the current collector used for the polarizable electrode mainly containing activated carbon include stainless steel, aluminum, titanium, and tantalum. Particularly preferred materials in terms of characteristics and cost of the resulting electric double-layer capacitor are stainless steel and aluminum. Preferred examples of the current collector used for the electrode mainly containing a carbon material that can reversibly occlude and release lithium ions include stainless steel, copper, and nickel.

The carbon material that can reversibly occlude and release lithium ions can be allowed to occlude lithium ions in advance by (1) a method of mixing powdery lithium to a carbon material that can reversibly occlude and release lithium ions, (2) a method of placing lithium foil on an electrode containing a carbon material that can reversibly occlude and release lithium ions and a binder so that the lithium foil is electrically in contact with the electrode, immersing this electrode in an electrolyte solution containing a lithium salt dissolved therein so that the lithium is ionized, and allowing the carbon material to take in the resulting lithium ions, or (3) a method of placing an electrode containing a carbon material that can reversibly occlude and release lithium ions and a binder on the minus side and placing a lithium metal on the plus side, immersing the electrodes in a non-aqueous electrolyte solution containing a lithium salt as an electrolyte, and supplying a current so that the carbon material is allowed to electrochemically take in the ionized lithium.

Examples of known electric double-layer capacitors include wound electric double-layer capacitors, laminated electric double-layer capacitors, and coin-type electric double-layer capacitors. The electric double-layer capacitor in the present invention may also be any of these types.

For example, a wound electric double-layer capacitor is assembled by winding a positive electrode and a negative electrode each of which includes a laminate (electrode) of a current collector and an electrode layer, and a separator in between to provide a wound element, putting this wound element in a case made of, for example, aluminum, filling the case with an electrolyte solution, preferably a non-aqueous electrolyte solution, and sealing the case with a rubber sealant.

In the present invention, a separator formed from a conventionally known material and having a conventionally known structure can also be used. Examples thereof include polyethylene porous membranes, and nonwoven fabric of polypropylene fiber, glass fiber, or cellulose fiber.

In accordance with any known method, the capacitor may be formed into a laminated electric double-layer capacitor in which a sheet-like positive electrode and negative electrode are stacked with an electrolyte solution and a separator in between or a coin-type electric double-layer capacitor in which a positive electrode and a negative electrode are fixed by a gasket with an electrolyte solution and a separator in between.

As mentioned above, the electrolyte solution of the present invention is useful as an electrolyte solution for large-size lithium ion secondary batteries for hybrid vehicles or distributed generation, and for electric double-layer capacitors.

EXAMPLES

Next, the present invention is described with reference to examples, but the present invention is not limited to these examples.

Examples and Comparative Examples (Preparation of Electrolyte Solution)

The components were mixed in accordance with the compositions shown in Tables 1 to 3, and LiPF$_6$ was added to each mixture to a concentration of 1.0 mol/L, thus obtaining non-aqueous electrolyte solutions.

The compounds in the tables are as follows.

Components (A)

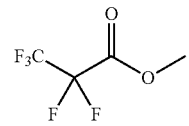

A-1

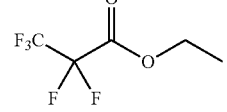

A-2

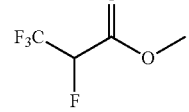

A-3

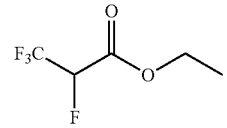

A-4

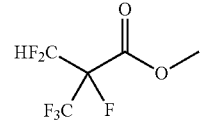

A-5

-continued
A-6 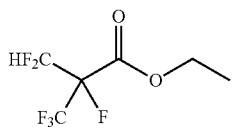
A-7 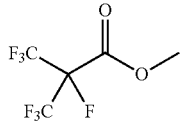
A-8 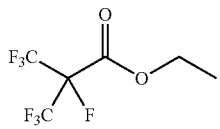
A-9 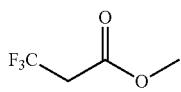
A-10 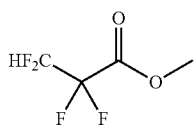
A-11 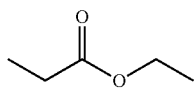
A-12
Components (B)
B-1 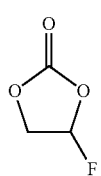
B-2 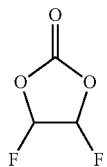
B-3 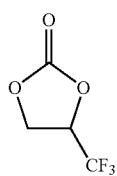
B-4 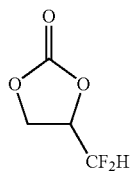
-continued
B-5 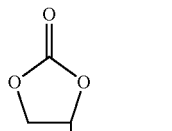
B-6 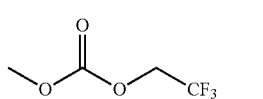
B-7 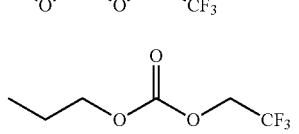
B-8 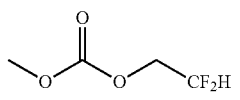
B-9 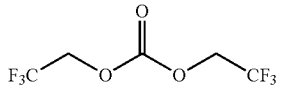
Components (C)
C-1 
C-2 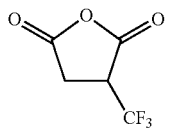
C-3 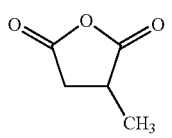
C-4 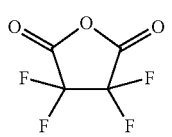
C-5 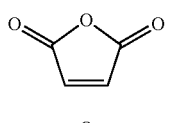
C-6 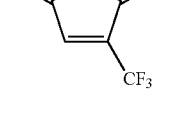
C-7 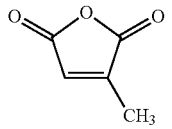

-continued

Other components

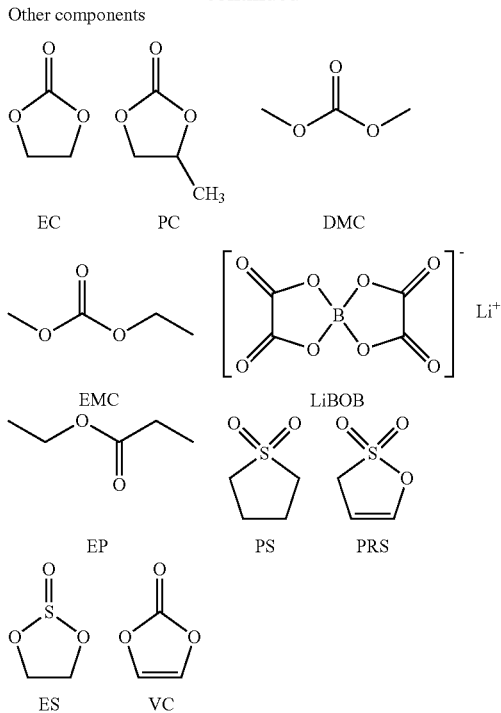

EC   PC   DMC   EMC   LiBOB   EP   PS   PRS   ES   VC (Production of Positive Electrode)

LiCoO$_2$ serving as a positive electrode active material, acetylene black serving as a conductive material, and dispersion of polyvinylidene fluoride (PVdF) in N-methyl-2-pyrrolidone serving as a binding agent were mixed such that the solid content ratio of the active material, the conductive material, and the binding agent was 92/3/5 (mass % ratio). Thereby, positive electrode mixture slurry was prepared. The resulting positive electrode mixture slurry was uniformly applied onto a 20-μm-thick aluminum foil current collector and dried, and then the workpiece was compression molded using a press. Thereby, a positive electrode was produced.

(Production of Negative Electrode)

Artificial graphite powder serving as a negative electrode active material, an aqueous dispersion of sodium carboxymethyl cellulose (concentration of sodium carboxymethyl cellulose: 1% by mass) serving as a thickening agent, and an aqueous dispersion of styrene-butadiene rubber (concentration of styrene-butadiene rubber: 50% by mass) serving as a binding agent were mixed into a slurry-like form in an aqueous solvent such that the solid content ratio of the negative electrode active material, the thickening agent, and the binding agent was 97.6/1.2/1.2 (mass % ratio). Thereby, negative electrode mixture slurry was prepared. The slurry was uniformly applied to 20-μm-thick copper foil and dried, and then the workpiece was compression molded using a press. Thereby, a negative electrode was produced.

(Production of Lithium Ion Secondary Battery)

The negative electrode and positive electrode produced as mentioned above and a polyethylene separator were stacked in the order of the negative electrode, the separator, and the positive electrode, whereby a battery element was produced.

This battery element was inserted into a bag made from a laminate film consisting of an aluminum sheet (thickness: 40 μm) and resin layers covering the respective faces of the sheet, with the terminals of the positive electrode and the negative electrode protruding from the bag. Then, the bag was charged with one of the electrolyte solutions having the compositions shown in the tables and vacuum-sealed. Thereby, a sheet-like lithium ion secondary battery was produced.

(Capacity Retention)

Within three hours after the preparation the electrolyte solution, the above produced secondary battery in the state of being sandwiched and pressurized between plates was subjected to constant current-constant voltage charge (hereinafter, referred to as CC/CV charge) (0.1 C cut off) to 4.5 V at a current corresponding to 0.2 C at 60° C. Then, the battery was discharged to 3 V at a constant current of 0.2 C. This process was counted as one cycle. The initial discharge capacity was determined from the discharge capacity of the third cycle. Here, 1 C means a current value required for discharging the reference capacity of a battery in an hour. For example, 0.2 C indicates a 1/5 current value thereof. The cycle was again repeated, and the discharge capacity after 150 cycles was defined as the capacity after cycles. The ratio of the discharge capacity after 150 cycles to the initial discharge capacity was determined, which was regarded as the capacity retention (%).

Capacity retention (%)=(Discharge capacity after 150 cycles)/(Initial discharge capacity)×100

(Gas Volume)

The volume of each of the produced lithium ion secondary batteries and the volume of each of the lithium ion secondary batteries after 150 cycles were measured to determine the gas volume (ml) by the following formula.

Gas volume (ml)=(Volume after 150 cycles)−(Initial volume)

(Storage of Electrolyte Solution)

The prepared electrolyte solutions were each enclosed in a stainless steel bottle, followed by storage in a constant-temperature bath at 45° C. for one week (168 hours), thus obtaining stored electrolyte solutions. Using the stored electrolyte solutions, the capacity retention and the gas volume were measured for each of the lithium ion secondary batteries produced by the above production method.

Tables 1 to 3 show the results.

TABLE 1

|  |  | Example 1 | Example 2 | Example 3 | Example 4 | Example 5 | Example 6 | Example 7 | Example 8 |
|---|---|---|---|---|---|---|---|---|---|
| Electrolyte solution composition | Component (A) |  |  |  |  |  |  |  |  |
|  | Type | A-3 | A-3 | A-3 | A-3 | A-3 | A-3 | A-3 | A-3 |
|  | Percentage (mass %) | 65 | 65 | 65 | 60 | 60 | 65 | 65 | 65 |
|  | Component (B) |  |  |  |  |  |  |  |  |
|  | Type | B-3 | B-3 | B-3 | B-4 | B-5 | B-3 | B-3 | B-3 |
|  | Percentage (mass %) | 33 | 33 | 33 | 38 | 38 | 33 | 33 | 32 |

TABLE 1-continued

|  |  |  |  |  |  |  |  |  |  |
|---|---|---|---|---|---|---|---|---|---|
|  |  | Component (C) |  |  |  |  |  |  |  |
|  |  | Type | C-1 1.5 | C-1 1.8 | C-2 1 | C-1 1.5 | C-1 1.5 | C-3 1.5 | C-4 1.9 | C-1 2 |
|  |  | Percentage (mass %) | C-5 0.5 | C-6 0.2 | C-5 1 | C-5 0.5 | C-5 0.5 | C-5 0.5 | C-5 0.1 | C-7 1 |
|  |  | Other component |  |  |  |  |  |  |  |  |
|  |  | Type | — | — | — | — | — | — | — | — |
|  |  | Percentage (mass %) |  |  |  |  |  |  |  |  |
| Battery characteristics | Electrolyte solution immediately after preparation | Capacity retention (%) | 94 | 91 | 9 | 90 | 87 | 88 | 89 | 88 |
|  |  | Gas production (ml) | 2.1 | 2.2 | 2.2 | 2.4 | 2.1 | 2.1 | 2.1 | 2.3 |
|  | Electrolyte solution after storage | Capacity retention (%) | 93 | 90 | 88 | 86 | 87 | 87 | 88 | 86 |
|  |  | Gas production (ml) | 2.2 | 2.2 | 2.3 | 2.7 | 2.3 | 2.1 | 2.2 | 2.4 |

|  |  |  | Example 9 | Example 10 | Example 11 | Example 12 | Example 13 | Example 14 | Example 15 |
|---|---|---|---|---|---|---|---|---|---|
| Electrolyte solution composition | Component (A) |  |  |  |  |  |  |  |  |
|  |  | Type | A-3 | A-1 | A-5 | A-3 | A-3 | A-3 | A-3 |
|  |  | Percentage (mass %) | 65 | 65 | 55 | 60 | 58 | 48 | 60 |
|  | Component (B) |  |  |  |  |  |  |  |  |
|  |  | Type | B-3 | B-7 | B-8 | B-9 | B-3 | B-3 20 B-6 | B-3 |
|  |  | Percentage (mass %) | 33 | 23 | 23 | 23 | 20 | 30 | 39 |
|  | Component (C) |  |  |  |  |  |  |  |  |
|  |  | Type | C-1 1.5 | C-1 1.5 | C-1 1.5 | C-1 1 | C-1 1.5 | C-1 1.5 | C-1 0.9 |
|  |  | Percentage (mass %) | C-7 0.5 | C-7 0.5 | C-3 0.5 | C-7 1 | C-5 0.5 | C-5 0.5 | C-3 0.1 |
|  | Other component |  |  |  |  |  |  |  |  |
|  |  | Type | — | EC | EC | EC | EMC | — | — |
|  |  | Percentage (mass %) |  | 10 | 20 | 15 | 20 |  |  |
| Battery characteristics | Electrolyte solution immediately after preparation | Capacity retention (%) | 88 | 85 | 70 | 83 | 80 | 84 | 73 |
|  |  | Gas production (ml) | 2.3 | 2.4 | 2.6 | 2.3 | 3.1 | 2.3 | 2.9 |
|  | Electrolyte solution after storage | Capacity retention (%) | 86 | 84 | 66 | 80 | 77 | 80 | 65 |
|  |  | Gas production (ml) | 2.4 | 2.5 | 2.9 | 2.5 | 3.4 | 2.6 | 3.2 |

TABLE 2

|  |  |  | Example 16 | Example 17 | Example 18 | Example 19 | Example 20 | Example 21 | Example 22 | Example 23 |
|---|---|---|---|---|---|---|---|---|---|---|
| Electrolyte solution composition | Component (A) |  |  |  |  |  |  |  |  |  |
|  |  | Type | A-3 | A-4 | A-4 | A-4 | A-3 | A-3 | A-3 | A-3 |
|  |  | Percentage (mass %) | 60 | 60 | 60 | 60 | 60 | 60 | 60 | 60 |
|  | Component (B) |  |  |  |  |  |  |  |  |  |
|  |  | Type | B-3 | B-3 | B-3 | B-3 | B-3 | B-3 | B-3 | B-3 |
|  |  | Percentage (mass %) | 39 | 39 | 38 | 38 | 39 | 39 | 39 | 39 |
|  | Component (C) |  |  |  |  |  |  |  |  |  |
|  |  | Type | C-4 0.95 C-6 | C-1 0.98 C-6 | C-5 1 C-7 | C-1 1 | C-2 1 | C-3 1 | C-4 1 | C-5 1 |
|  |  | Percentage (mass %) | 0.05 | 0.02 | 1 |  |  |  |  |  |

TABLE 2-continued

|  |  |  |  |  |  |  |  |  |  |
|---|---|---|---|---|---|---|---|---|---|
|  |  | Other component |  |  |  |  |  |  |  |
|  |  | Type | — | — | — | LiBOB | — | — | — | — |
|  |  | Percentage (mass %) |  |  |  | 1 |  |  |  |  |
| Battery characteristics | Electrolyte solution immediately after preparation | Capacity retention (%) | 78 | 77 | 69 | 71 | 70 | 71 | 70 | 72 |
|  |  | Gas production (ml) | 2.6 | 2.8 | 3.3 | 3.4 | 3.4 | 3.3 | 3.3 | 3.4 |
|  | Electrolyte solution after storage | Capacity retention (%) | 76 | 75 | 66 | 66 | 67 | 65 | 65 | 66 |
|  |  | Gas production (ml) | 2.6 | 3.0 | 3.7 | 3.6 | 3.6 | 3.5 | 3.6 | 3.4 |

|  |  |  | Example 24 | Example 25 | Example 26 | Example 27 | Example 28 | Example 29 | Example 30 |
|---|---|---|---|---|---|---|---|---|---|
| Electrolyte solution composition | Component (A) |  |  |  |  |  |  |  |  |
|  |  | Type | A-3 | A-3 | A-2 | A-5 | A-6 | A-7 | A-8 |
|  |  | Percentage (mass %) | 60 | 60 | 60 | 60 | 60 | 60 | 60 |
|  | Component (B) |  |  |  |  |  |  |  |  |
|  |  | Type | B-3 | B-3 | B-3 | B-3 | B-3 | B-3 | B-3 |
|  |  | Percentage (mass %) | 39 | 39 | 39 | 39 | 39 | 39 | 39 |
|  | Component (C) |  |  |  |  |  |  |  |  |
|  |  | Type | C-6 | C-7 | C-1 | C-1 | C-1 | C-1 | C-1 |
|  |  | Percentage (mass %) | 1 | 1 | 1 | 1 | 1 | 1 | 1 |
|  | Other component |  |  |  |  |  |  |  |  |
|  |  | Type | — | — | — | — | — | — | — |
|  |  | Percentage (mass %) |  |  |  |  |  |  |  |
| Battery characteristics | Electrolyte solution immediately after preparation | Capacity retention (%) | 69 | 66 | 68 | 67 | 67 | 67 | 66 |
|  |  | Gas production (ml) | 3.3 | 3.3 | 3.5 | 3.4 | 3.6 | 3.7 | 3.8 |
|  | Electrolyte solution after storage | Capacity retention (%) | 65 | 63 | 64 | 63 | 66 | 64 | 63 |
|  |  | Gas production (ml) | 3.5 | 3.5 | 3.6 | 3.5 | 3.5 | 3.8 | 3.9 |

TABLE 3

|  |  |  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|
| Electrolyte solution composition | Component (A) |  |  |  |  |  |  |  |  |
|  |  | Type | A-3 | A-1 | A-3 | A-3 | A-4 | A-5 | A-5 |
|  |  | Percentage (mass %) | 65 | 65 | 65 | 66 | 67 | 65 | 65 |
|  | Component (B) |  |  |  |  |  |  |  |  |
|  |  | Type | B-1 | B-1 | B-1 | B-1 | B-2 | B-3 | B-3 |
|  |  | Percentage (mass %) | 35 | 34 | 32 | 32 | 31 | 33 | 32 |
|  | Component (C) |  |  |  |  |  |  |  |  |
|  |  | Type | — | — | — | — | — | — | — |
|  |  | Percentage (mass %) |  |  |  |  |  |  |  |
|  | Other component |  |  |  |  |  |  |  |  |
|  |  | Type | — | LiBOB | PS | PRS | ES | VC | LiBOB VC |
|  |  | Percentage (mass %) |  | 1 | 3 | 2 | 2 | 2 | 1 2 |
| Battery characteristics | Electrolyte solution immediately after preparation | Capacity retention (%) | 55 | 64 | 58 | 56 | 55 | 58 | 60 |
|  |  | Gas production (ml) | 4.1 | 3.9 | 3.8 | 3.6 | 4.4 | 5.1 | 4.8 |

TABLE 3-continued

|  |  |  |  |  |  |  |  |  |  |
|---|---|---|---|---|---|---|---|---|---|
| Electrolyte solution after storage | Capacity retention (%) | 18 | 30 | 24 | 31 | 27 | 22 | 28 |  |
|  | Gas production (ml) | 4.9 | 5.1 | 5.5 | 5.1 | 5.3 | 6.2 | 6.1 |  |

|  |  |  | Comparative Example 8 | Comparative Example 9 | Comparative Example 10 | Comparative Example 11 | Comparative Example 12 | Comparative Example 13 | Comparative Example 14 |
|---|---|---|---|---|---|---|---|---|---|
| Electrolyte solution composition | Component (A) |  |  |  |  |  |  |  |  |
|  |  | Type | A-3 | A-4 | A-2 | A-1 | A-8 | A-9 | A-10 |
|  |  | Percentage (mass %) | 50 | 50 | 70 | 60 | 60 | 60 | 60 |
|  | Component (B) |  |  |  |  |  |  |  |  |
|  |  | Type | B-6 | — | — | — | — | B-1 | B-1 |
|  |  | Percentage (mass %) | 20 |  |  |  |  | 38 | 15 |
|  | Component (C) |  |  |  |  |  |  |  |  |
|  |  | Type | — | C-1 | C-1 | C-5 | C-1 C-5 | C-1 | C-1 |
|  |  | Percentage (mass %) |  | 1 | 2 | 1 | 1 1 | 2 | 2 |
|  | Other component |  |  |  |  |  |  |  |  |
|  |  | Type | EC | EC | EC | EC | EC | — | EC |
|  |  | Percentage (mass %) | 28 VC 2 | 30 EP 18 VC 1 | 20 PC 8 | 39 | 38 |  | 23 |
| Battery characteristics | Electrolyte solution immediately after preparation | Capacity retention (%) | 51 | 50 | 49 | 50 | 47 | 44 | 47 |
|  |  | Gas production (ml) | 5.5 | 6.1 | 5.5 | 4.5 | 4.4 | 4.5 | 4.3 |
|  | Electrolyte solution after storage | Capacity retention (%) | 31 | 22 | 24 | 27 | 23 | 22 | 21 |
|  |  | Gas production (ml) | 7.1 | 7.5 | 6.8 | 5.2 | 5.5 | 5.1 | 5.3 |

|  |  |  | Comparative Example 15 | Comparative Example 16 | Comparative Example 17 | Comparative Example 18 | Comparative Example 19 |
|---|---|---|---|---|---|---|---|
| Electrolyte solution composition | Component (A) |  |  |  |  |  |  |
|  |  | Type | A-11 | A-12 | A-1 | A-9 | — |
|  |  | Percentage (mass %) | 60 | 60 | 50 | 40 |  |
|  | Component (B) |  |  |  |  |  |  |
|  |  | Type | B-1 | B-1 | — | B-1 | — |
|  |  | Percentage (mass %) | 35 | 38 |  | 2 |  |
|  | Component (C) |  |  |  |  |  |  |
|  |  | Type | C-1 | C-1 | — | — | C-1 |
|  |  | Percentage (mass %) | 2 | 2 |  |  | 2 |
|  | Other component |  |  |  |  |  |  |
|  |  | Type | — | — | EC PC LiBOB | EC DMC | EC EP |
|  |  | Percentage (mass %) |  |  | 40 9 1 | 30 28 | 30 68 |
| Battery characteristics | Electrolyte solution immediately after preparation | Capacity retention (%) | 45 | 47 | 47 | 41 | 38 |
|  |  | Gas production (ml) | 4.6 | 4.8 | 4.9 | 5.1 | 5.3 |
|  | Electrolyte solution after storage | Capacity retention (%) | 26 | 31 | 26 | 20 | 11 |
|  |  | Gas production (ml) | 5.6 | 6.0 | 6.2 | 7.1 | 7.7 |

The invention claimed is:

1. An electrolyte solution comprising:
a lithium salt;
a compound (1) represented by following formula (1):
$$CF_3CFX^{11}COOR^{11} \quad (1),$$
wherein, in formula (1), $X^{11}$ is a hydrogen atom, or a C1-C3 alkyl group in which one or more hydrogen atoms are optionally replaced by fluorine atoms; and $R^{11}$ is a C1-C3 alkyl group in which one or more hydrogen atoms are optionally replaced by fluorine atoms;
a fluorinated carbonate;
a compound (2) represented by following formula (2); and
a compound (3) represented by following formula (3);
wherein the electrolyte solution contains the compound (2) and the compound (3) in amounts of 0.08 to 2.50% by mass and 0.02 to 1.50% by mass, respectively, relative to the electrolyte solution,
wherein the fluorinated carbonate is at least one selected from the group consisting of a fluorinated acyclic carbonate and a fluorinated saturated cyclic carbonate compound represented by following formula (A);

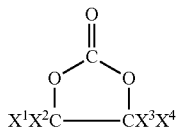
(A)

wherein, in formula (A), $X^1$ to $X^4$ are the same as or different from each other and are each —H, —C, —O, or —F, a fluorinated alkyl group optionally having an ether bond, or a fluorinated alkoxy group optionally having an ether bond; at least one of $X^1$ to $X^4$ is —F, a fluorinated alkyl group optionally having an ether bond, or a fluorinated alkoxy group optionally having an ether bond,

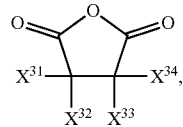
(2)

wherein, in formula (2), $X^{31}$ to $X^{34}$ are the same as or different from each other and are each a group containing at least H, C, O, or F,

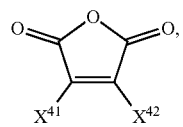
(3)

wherein in formula (3), $X^{41}$ and $X^{42}$ are the same as or different from each other and are each a group containing at least H, C, O, or F.

2. An electrochemical device comprising:
the electrolyte solution according to claim 1.

3. A module comprising:
the electrochemical device according to claim 2.

4. A lithium ion secondary battery comprising:
the electrolyte solution according to claim 1.

5. A module comprising:
the lithium ion secondary battery according to claim 4.

* * * * *